(12) United States Patent
Shiibashi

(10) Patent No.: US 10,565,349 B2
(45) Date of Patent: Feb. 18, 2020

(54) CLOUD-TO LOCAL, LOCAL-TO-CLOUD SWITCHING AND SYNCHRONIZATION OF MEDICAL IMAGES AND DATA

(71) Applicant: Konica Minolta Healthcare Americas, Inc., Wayne, NJ (US)

(72) Inventor: Takao Shiibashi, Wayne, NJ (US)

(73) Assignee: Konica Minolta Healthcare Americas, Inc., Wayne, NJ (US)

( * ) Notice: Subject to any disclaimer, the term of this patent is extended or adjusted under 35 U.S.C. 154(b) by 169 days.

(21) Appl. No.: 15/699,181

(22) Filed: Sep. 8, 2017

(65) Prior Publication Data

US 2019/0080053 A1    Mar. 14, 2019

(51) Int. Cl.
| | | |
|---|---|---|
| *G06F 9/445* | (2018.01) | |
| *G06F 19/00* | (2018.01) | |
| *H04L 29/08* | (2006.01) | |
| *G06F 16/23* | (2019.01) | |
| *G16H 10/60* | (2018.01) | |
| *G06F 8/65* | (2018.01) | |
| *G06F 16/27* | (2019.01) | |
| *G16H 30/20* | (2018.01) | |
| *G06F 16/178* | (2019.01) | |

(52) U.S. Cl.
CPC ............. *G06F 19/32* (2013.01); *G06F 8/65* (2013.01); *G06F 16/178* (2019.01); *G06F 16/23* (2019.01); *G06F 16/27* (2019.01); *G16H 10/60* (2018.01); *G16H 30/20* (2018.01); *H04L 67/1095* (2013.01); *H04L 67/325* (2013.01)

(58) Field of Classification Search
CPC ..... G06F 8/65; G06F 8/67; G06F 8/68; G06F 11/1433; G06F 8/60
USPC .................................................. 717/168–178
See application file for complete search history.

(56) References Cited

U.S. PATENT DOCUMENTS

| | | | |
|---|---|---|---|
| 2014/0201145 A1* | 7/2014 | Dorman ................. | G06F 16/27 707/634 |
| 2018/0150632 A1* | 5/2018 | Sharma ................. | G06F 21/45 |
| 2018/0218119 A1* | 8/2018 | Ueda ................. | G06F 21/6245 |
| 2019/0080054 A1* | 3/2019 | Shiibashi ............. | G06F 19/321 |

FOREIGN PATENT DOCUMENTS

| | | |
|---|---|---|
| JP | 2006-189973 A | 7/2006 |
| JP | 2012-59080 A | 3/2012 |

* cited by examiner

*Primary Examiner* — Chuck O Kendall
(74) *Attorney, Agent, or Firm* — Osha Liang LLP

(57) ABSTRACT

A method for updating a system that synchronizes medical data between a cloud repository on a cloud server and a plurality of local repositories on a plurality of local servers of healthcare facilities connected to the cloud server is provided. The method includes, by the cloud server: receiving a request to update a medical synchronization application stored on the cloud server and each of the local servers of the healthcare facilities using an update file; transmitting an instruction to each local server to update the medical synchronization application determining a version information of the medical synchronization application on all of the local servers; and executing the update file to update the medical synchronization application on the cloud server only in the event that cloud server determines that the medical synchronization application of all of the local servers have been updated.

20 Claims, 23 Drawing Sheets

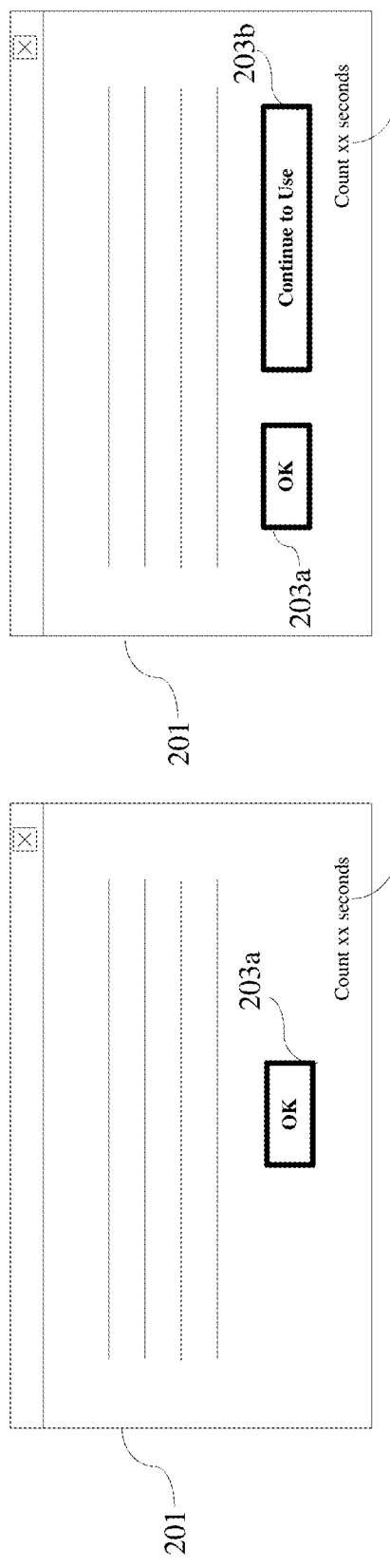

Main GUI
800

<Application Update Scheduler>

Available Version   | -------------- ▽ |

Date & Time   | Day / Month / Year    Time |

Warning Message

|  |
|  |

| Clear |        | Schedule |

<Medical Servers>
Update Process Status: -

| Server Name | Facility No. | Version | Update File Download | Update Status |
|---|---|---|---|---|
| Cloud | ---------- | V200R00 | ---------- | ---- |
| HSP 1 | AAAAAA | V200R00 | ---------- | ---- |
| Clinic 1 | BBBBBB | V200R00 | ---------- | ---- |
| Clinic 2 | CCCCCC | V200R00 | ---------- | ---- |

| Functional Item | | | | |
|---|---|---|---|---|
| 100 Connection Monitoring | 101 Check the connection to cloud periodically | Periodically Monitor/Check if the application proxy server (APS) can connect to cloud properly | Monitor/Check interval. Default 10 secs (System level) | |
| 200 Connection Error (Detection) | 201 Timeout | Specify the timeout value for network connection | Timeout setting. Default 3 secs (System level) | |
| | 203 Number of Failures | Detect as connection is lost with continuous number of timeouts or another general network error | Number of connection test failure to detect connection is lost. Default 3 times (System level) | |
| 300 Connection Error (Notification) | 301 Notify the connection error | Notification is sent to all the local computers connected to the APS | | |
| | 302 Display message to try to re-connect the cloud server | Notification is sent to all the local computers connected to the APS and a message is displayed to inform user that reconnection attempts will be made for pre-defined time. The user cannot use the application while this message is displayed. The system will operate normally if network connection is recovered during this message is displayed, but the message 303 is displayed if recovery attempts fail. Example message: "Connection to the cloud server has been lost. System trying to re-connect to the cloud server." | Time setting to display this message. Default 20 secs (System level) | |
| | 303 Display message to change the connection from cloud to local | Notification is sent to all the local computers connected to the APS and a message is displayed to inform the user that the connection will be switched from cloud to local. Example message: "Connection to the cloud server has been lost. System connects from cloud to local. Please depress the OK button to close the application. Otherwise the application is forcefully closed after xx seconds." | | |
| | 304 Forced Termination | The application is forcefully closed after the message is displayed and pre-defined time has passed | Timeout setting for application forced close. Default 60 secs (System level) | |
| | 305 Application startup prohibition | Once the network failure occurs between cloud and APS, and the application running on the local computer connected to the APS has not been closed with 303 or 304 logic, users on those local computers cannot start the application | | |
| 400 Change the connection from cloud to local | 401 Change the connection from cloud to local | Once the network failure occurs on an APS and no application is running on the APS, the application automatically starts and login screen is displayed on the local computers on which the application was closed with 302 or 303 logic | | |

FIG. 13A

| Functional Item | | | Description |
|---|---|---|---|
| Constrains while connected to the local | 501 Constrains while connected the local | | Editing/modifying/deleting of the existing information is prohibited to avoid conflict. However, new data can be added.<br><br><Patient Screen><br>- User can add patient<br>- User can edit newly added patient<br>- User cannot edit any information for existing patient<br><br><Viewer/Report Screen><br>- User can open viewer screen<br>- User can operate viewer function but nothing is saved (ex.) annotation/measurement, window level, flip, rotate, zoom, etc.<br>- User can create new report<br>- User can edit newly added report<br>- User cannot edit existing report<br><br><Input Data><br>- System can get only image data (ex.) DICOM images, general images<br>- System refuse to get other data (ex.) HL7 order, Labo/Vital data, etc.<br><br><Settings><br>- User cannot add/modify/delete any settings |
| Connection recovered | 601 | Connection confirmation | Detect as connection is recovered with continuous number of connection test success | Number of connection test success to detect connection is recovered. Default 2 times (System level) |
| | 602 | Notify the connection recovered | Notification is sent to all the local computer connected to the APS and a message is displayed for user to notify the connection will be changed from local to cloud.<br>"Connection to the cloud server has been recovered. System connects from local to cloud. Please depress the OK button to close the application. Or, you can choose to continue to use application. The application is forcefully closed after xx seconds without selection."<br>* The data in middle of input is saved when application is closed. | |
| | 603 | Forced termination | The application is forcefully closed after the message is displayed and then pre-defined time is passed<br>* The data in middle of input is saved when application is closed. | Same as 602 |
| | 604 | Application startup prohibition | Once the network connection recover between cloud and APS and the application running on the local computer which is connected to the APS has not been closed with 602 or 603 logic, any user on those local computer cannot start the application | |

FIG. 13B

| Functional Item | | |
|---|---|---|
| Switch the connection from local to cloud | 701 Switch the connection from local to cloud | Once the network's connection is recovered on an APS, application is running on the APS. Application automatically starts on the local computers on which the application was closed with 602 or 603 logic. At this moment, the message "Synchronizing…" is displayed until the synchronization process is done, and user cannot execute or operate the application during that time. Once the synchronization process is done, then login screen is displayed |
| Synchronization (Upload) | 851 Synchronization between local and cloud | Once the network connection is recovered between local and cloud, synchronization process from local to cloud begin to update the information that is added on local side while the connection has been lost |

FIG. 13C

CLOUD-TO LOCAL, LOCAL-TO-CLOUD SWITCHING AND SYNCHRONIZATION OF MEDICAL IMAGES AND DATA

BACKGROUND

Medical images and medical data play a crucial role in the diagnosis of a patient. Healthcare facilities (e.g., hospitals) have realized the benefits of electronically storing medical images and medical data. The digitalization of the medical images and data not only enables users to easily access medical images and medical data, but also enables the images and data to be easily shared between multiple healthcare facilities.

In the healthcare industry, the use of a system known as a Picture Archiving and Communications System ("PACS") is becoming increasing popular for convenient storage and access of medical images. Generally, PACS comprises a multitude of devices working cooperatively to digitally capture, store, manage, distribute, and display medical images generated by various imaging modalities, such as computed tomography (CT), magnetic resonance imaging (MRI), position emission tomography (PET), ultrasound, X-ray, etc. PACS allows various healthcare facilities to share all types of images captured internally or externally.

More recently, cloud-based PACS have emerged as a way to improve efficiency and accessibility of traditional PACS. In general, a "cloud" can be understood as an online storage system that provides remote, on-demand access of computing resources and data over the Internet to multiple computers and devices in various locations. Cloud-based PACS may be provided by vendors who use remote or off-site data centers in various locations for storage of medical images.

SUMMARY

In general, in one aspect, the invention relates to a method for updating a system that synchronizes medical data between a cloud repository on a cloud server and a plurality of local repositories on a plurality of local servers of healthcare facilities connected to the cloud server. The method comprises: receiving, by the cloud server, a request to update a medical synchronization application stored on the cloud server and each of the local servers of the healthcare facilities using an update file; transmitting, by the cloud server to each of the local servers, an instruction to update the medical synchronization application, wherein the instruction includes the update file; determining, by the cloud server, a version information of the medical synchronization application on all of the local servers; and executing, by the cloud sever, the update file to update the medical synchronization application on the cloud server only in the event that cloud server determines that the medical synchronization application of all of the local servers have been updated; and in response to one of the plurality of local servers establishing a connection with the cloud server, causing the cloud server to: determine the version information of the medical synchronization application of the local server establishing the connection; and in the event that the version information of the medical synchronization application of the local server establishing the connection is different from the version information of the medical synchronization application on the cloud server, transmit the instruction to update the medical synchronization application to the local server establishing the connection.

In general, in one aspect, the invention relates to a non-transitory computer-readable medium (CRM) storing instructions that cause a cloud server coupled to a computer to perform an operation to update a system that synchronizes medical data between a cloud repository on the cloud server and a plurality of local repositories on a plurality of local servers of healthcare facilities connected to the cloud server. The operation comprises: receiving, by the cloud server, a request to update a medical synchronization application stored on the cloud server and each of the local servers of the healthcare facilities using an update file; transmitting, by the cloud server to each of the local servers, an instruction to update the medical synchronization application, wherein the instruction includes the update file; determining, by the cloud server, a version information of the medical synchronization application on all of the local servers; and executing, by the cloud sever, the update file to update the medical synchronization application on the cloud server only in the event that cloud server determines that the medical synchronization application of all of the local servers have been updated; and in response to one of the plurality of local servers establishing a connection with the cloud server, causing the cloud server to: determine the version information of the medical synchronization application of the local server establishing the connection; and in the event that the version information of the medical synchronization application of the local server establishing the connection is different from the version information of the medical synchronization application on the cloud server, transmit the instruction to update the medical synchronization application to the local server establishing the connection.

In general, in one aspect, the invention relates to a system that synchronizes medical data. The system comprises: a cloud server; a cloud repository on the cloud server; and a plurality of local repositories on a plurality of local servers of healthcare facilities connected to the cloud server, wherein the cloud server: receives a request to update a medical synchronization application stored on the cloud server and each of the local servers using an update file, transmits, to each of the local servers, an instruction to update the medical synchronization application, wherein the instruction includes the update file, determines, a version information of the medical synchronization application on all of the local servers, and executes the update file to update the medical synchronization application on the cloud server only in the event that cloud server determines that the medical synchronization application of all of the local servers have been updated, and wherein, in response to one of the plurality of local servers establishing a connection with the cloud server, the cloud server: determines the version information of the medical synchronization application of the local server establishing the connection, and in the event that the version information of the medical synchronization application of the local server establishing the connection is different from the version information of the medical synchronization application on the cloud server, transmits the instruction to update the medical synchronization application to the local server establishing the connection.

Other aspects and advantages of the invention will be apparent from the following description and the appended claims.

BRIEF DESCRIPTION OF DRAWINGS

FIGS. 2A and 2B show a display message in accordance with one or more embodiments.

FIG. 3 shows a data table in accordance with one or more embodiments.

FIGS. 13A, 13B, and 13C show an implementation example in accordance with one or more embodiments.

DETAILED DESCRIPTION

Figure 1A:
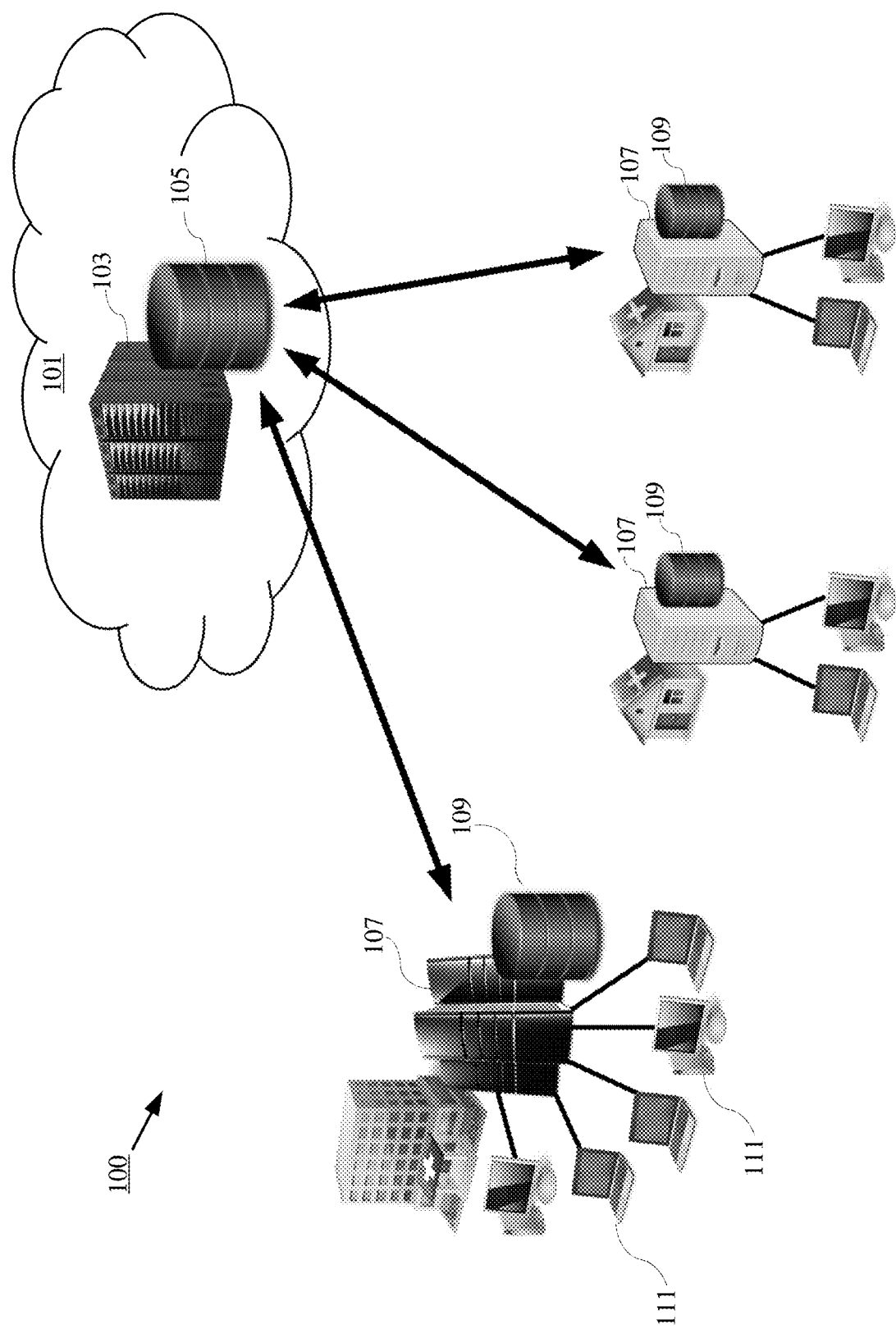
FIGS. 1A and 1B show a system in accordance with one or more embodiments.

Specific embodiments will now be described in detail with reference to the accompanying figures. Like elements in the various figures are denoted by like reference numerals for consistency. Like elements may not be labeled in all figures for the sake of simplicity.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that, one or more of the steps shown in the flowcharts may be omitted, repeated, and/or performed in a different order than the order shown. Accordingly, the scope of the invention should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

In general, one or more embodiments of the invention provide a method, a non-transitory computer readable medium, and a system configured for cloud-to-local, local-to-cloud switching and synchronization of medical images and data with a mechanism for automatically performing a system update and checking for application version mismatch. The cloud-based PACS in accordance with one or more embodiments enables all healthcare facilities that are given permission to access a cloud data repository or database ("cloud repository"), such as facilities within the same hospital group, to share medical images and data. The medical images and data may also include a patient's medical reports. For example, a healthcare facility would be able to access and retrieve its patients' medical images and data obtained at the other healthcare facilities that are "in-network" (i.e., having permission to access the same portion of the cloud repository). Specifically, according to one or more embodiments, in-network healthcare facilities can more effectively utilize cloud-based PACS to share and update medical images and data for patients who frequent more one or more of the in-network healthcare facilities.

Moreover, unlike conventional cloud-based PACS, one or more embodiments of the invention enable a healthcare facility that utilizes cloud-based PACS to remain operational even when a network connection between the healthcare facility and the cloud is disconnected. Specifically, in-network healthcare facilities that utilize one or more embodiments are able to automatically keep on-site or local data repositories or databases ("local repositories") on a local server updated with the most recent patient images and data stored in the cloud repository based on a need of the users of the cloud-based PACS (e.g., healthcare professionals). For example, if one facility updates or obtains a new medical image of a particular patient, the cloud repository may be automatically updated with the updated or new medical image, and all the local repositories of the in-network facilities that treat or care for that same patient may be automatically synchronized with the cloud repository.

In one or more embodiments, in the event of a loss of connection, the disconnected healthcare facilities automatically switch access to the local repositories instead of the cloud repository. This enables the healthcare facilities to establish a continuous workflow without experiencing any downtime caused by the disconnection from the network. Because the local repositories of in-network facilities are synchronized with the cloud repository, the facilities are able to at least temporarily access and work with the most up-to-date data, even without connection to the cloud. However, not all the data on the cloud repository need necessarily be synchronized. In one or more embodiments, the synchronization occurs only with respect to data that is necessary or is of interest to the respective facilities. For example, a facility may not want its local repository filled or local server burdened with medical images related to people who are not patients of that facility.

In one or more embodiments, when the connection is reestablished, the medical images and data stored in the local repositories during the time of network disconnection are automatically uploaded to the cloud repository. This enables all of the other in-network healthcare facilities to update their respective local repositories with the most up-to-date medical images and data.

In one or more embodiments, the cloud-based PACS checks for version mismatch between a vendor-provided application installed on each connected device (i.e., the local servers and the cloud), and prevents two devices with different versions of the same vendor-provided application from synchronizing medical images and data. The version mismatch occurs when version information of the vendor-provided application stored on two different devices are different. The check for version mismatch ensures not only that the connected devices will be applying the same synchronization settings but also that the medical images and data synchronized between the connected devices are accurate and consistent. For example, a newer version of the vendor-provided application may include synchronization settings and medical images and data processing settings that are not available or different from the settings included in an older version of the same vendor-provided application. Therefore, synchronization errors or inconsistencies in the medical image and data may occur when synchronization of medical images and data between two servers installed with different versions of the vendor-provided application is initiated.

One or more embodiments operate without a predetermined update sequence for the updating of the medical synchronization application on the cloud server and the local servers. This enables the healthcare facilities to establish a continuous workflow in the event that a local server at one of the multiple healthcare facilities loses connection from the cloud when the cloud-based PACS system is updating the vendor-provided applications. For example, healthcare facilities that have completed the update of the vendor-provided application do not need to wait for the disconnected healthcare facility to complete the update of the vendor-provided application upon re-establishing connection with the cloud-based PACS system.

Figure 1B:
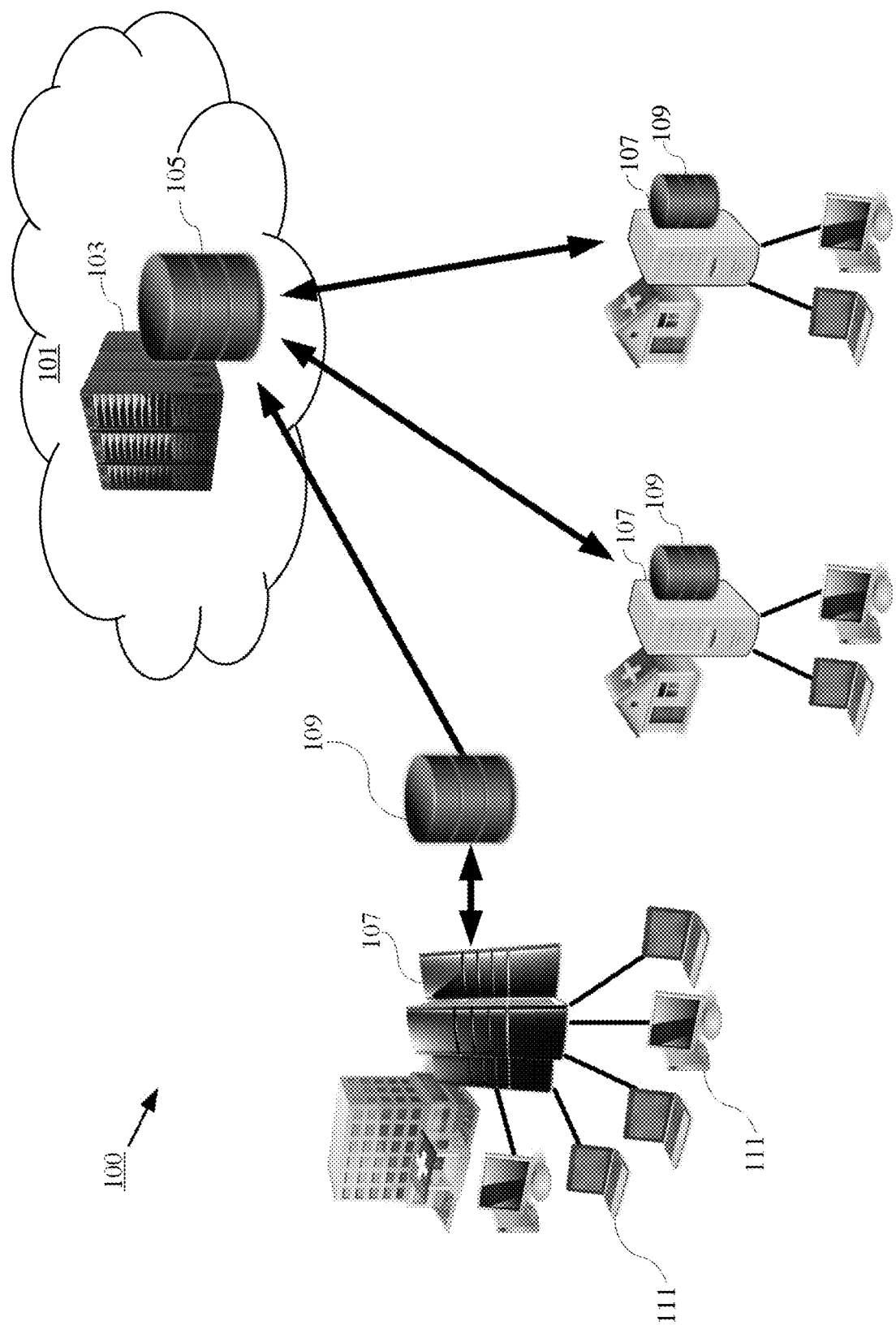

FIGS. 1A and 1B show a system (100) in accordance with one or more embodiments of the invention. As shown in FIGS. 1A and 1B, the system (100) includes a cloud (101) that includes a cloud server (103) with a cloud repository (105), and multiple local servers (107) (e.g., application proxy servers (APS)) and local repositories (109) associated with different in-network healthcare facilities (not labeled). The multiple local servers (107) are authorized to access/view the cloud server (103). In addition to the right to access the remote data on the cloud server (103), certain local servers (107) may also have the right to edit the remote data. Each of the healthcare facilities may be a type of facility that provides medical care such as a public hospital, a private hospital, a medical clinic, a dental clinic, etc.

As also shown in FIGS. 1A and 1B, each healthcare facility in the system (100) includes multiple user computing devices (111) (herein referred to as "a local computer") coupled to the local servers (107). Each local computer (111) may correspond to a personal computer (PC), a laptop, a mobile computing device (e.g., tablet PC, smartphone, etc.), a server, a mainframe, a kiosk, etc.

In one or more embodiments, the cloud server (103) with the cloud repository (105) may be operated by a vendor providing the cloud-based PACS or another third-party associated with such a vendor. In one or more embodiments, the cloud server (103) is a physical and/or virtual computing infrastructure that performs application and information processing. For example, the cloud server (103) may be a virtual server or a physical server accessed remotely via the Internet. In one or more embodiments, the cloud repository (105) is an online repository of data. For example, the cloud repository may be a virtual data room (VDR) or a database (or group of databases) accessed remotely via the Internet.

In one or more embodiments, the cloud server (103) is configured to receive the medical images and data transmitted from the local servers (107) and store the medical images and data in the cloud repository (105) as remote data.

In one or more embodiments, each local server (107) is operated by the associated healthcare facility. The local server (107) is configured to transmit the medical images and data received from the local computers (111) to the cloud repository (105) on the cloud server (103). Each local repository (109) is operated and maintained by the associated healthcare facility. The local repository (109) may locally store medical images and data received from the local server (107) and the cloud repository (105) local data.

In one or more embodiments, the local computers (111) are operated by medical professionals associated with the respective healthcare facilities and are configured to transmit to the local server (107) medical images and data taken from one or more modalities (not shown) in the healthcare facility. In one or more embodiments, the local computers (111) may be configured as the local server (107). In one or more embodiments, the local computers (111) may also include the local repository (109).

In one or more embodiments, the local computers are configured to store an application provided by the vendor that operates the cloud (101). In one or more embodiments, the application may be a medical synchronization application provided by a third-party associated with the vendor. The medical synchronization application may be an independent software application registered to the device (i.e., the cloud (101) or the local servers (107)) that the medical synchronization application is stored in or a web-browser based application with a graphical user interface ("GUI") that allows the local computers (111) to access the cloud (101) to synchronize medical data with the cloud (101).

In one or more embodiments, the cloud server (103) and each of the local servers (107) may store a copy of the medical synchronization application in the respective repositories. In one or more embodiments, information regarding the version of the medical synchronization application stored in each device may be viewed by the user or accessed by each device as version information of the medical synchronization application. For example, in one or more embodiments, the version information of the medical synchronization application may be presented as "The current version of the registered medical synchronization application is Ver. 1.01," or alternatively, as "Ver. 1.01."

In one or more embodiments, different versions of the medical synchronization application may be configured to include different synchronization settings and medical images and data processing settings. For example, a newer version of the medical synchronization application may store medical images and data using a different file type than an older version. Similarly, different versions of the medical synchronization application may have different settings for organizing and storing metadata included in the medical images and data. The metadata may include general patient information and diagnosis-related information for each of the patient's medical images or medical data.

In one or more embodiments, an authorized user associated with the vendor of the cloud-based PACS may schedule an update of the medical synchronization application stored in all of the servers connected within the system (100). In one or more embodiments, when a medical synchronization application is being updated on a local server (107) at one of the healthcare facilities, the users of the local computers (111) at that healthcare facility would not be able to use the medical synchronization application. When the medical synchronization application is being updated on the cloud server (103), none of the local servers (107) at the healthcare facilities would be able to access the functions of the cloud server (103).

When the local servers (107) cannot access the functions of the cloud server (103), the local servers (107) are unable to exchange (e.g., synchronize, transmit, retrieve) any medical images and data from the cloud server (103).

FIG. 1A shows an example in accordance with one or more embodiments where the connection between the in-network healthcare facilities and the cloud (101) is stable. In this state, the multiple in-network healthcare facilities may communicate bilaterally with the cloud (101). As shown in FIG. 1A, the in-network healthcare facilities may transmit locally-obtained medical images and data to the cloud (101) to be stored as remote data in the cloud repository (105) accessible to other in-network healthcare facilities. In one or more embodiments, the in-network healthcare facilities may retrieve medical images and data from the cloud (101) to be stored as local data in their respective local repositories (109).

In one or more embodiments, not all of the remote data stored in the cloud repository (105) need be retrieved by the in-network healthcare facilities to be stored as local data. The remote data to be retrieved and stored as local data may vary based on the size and need of the healthcare facility or on the preferences of the local computers (111) (e.g., healthcare professionals). For example, the remote data to be retrieved and stored as local data in the local repositories (109) of certain in-network healthcare facilities may be based on specific individuals who are patients of those facilities. Thus, if a particular individual is not a patient of a particular in-network healthcare facility, that healthcare facility may not retrieve and store that patient's medical images and data from the cloud (101) as local data. This option may be particularly useful for smaller healthcare facilities with smaller local servers (107) and local repositories (109) with limited storage and processing power. In one or more embodiments, the remote data to be retrieved and stored as local data in the local repositories (109) of certain in-network healthcare facilities may be based on a specific medical study, medical series, medical image, or medical report instead of being based on specific individuals who are patients of those facilities.

In one or more embodiments, users of the local computers (111) at each in-network healthcare facility may view the medical images and data stored on the cloud repository (105) through a web-browser based version of the application that is stored on the cloud sever (103). The user may also view the images through a local version of the application stored on the local computers (111). For example, healthcare professionals may determine if any of the local data stored in the local repository (109) has been updated by another healthcare professional associated with a different in-network healthcare facility, and retrieve the updated data from the cloud repository (105) to replace the current local data. In one or more embodiments, the updating of the local data may be performed automatically by the system (100), e.g., through the application stored on the local computers (111).

For example, an individual may be a patient at multiple in-network healthcare facilities. Each of these in-network healthcare facilities may store the individual's medical images and data as local data. In one or more embodiments, the individual's medical images and data are updated in the cloud repository (105) by one of the in-network healthcare facilities, the other in-network healthcare facilities where the individual is also a patient may automatically retrieve (synchronize) the individual's updated images and data to keep the local data in the local repository (109) up-to-date. The automatic updating of the cloud repository (105) and/or synchronization of the pertinent local repositories (109) may be triggered every time the individual's medical images or data are updated on the cloud, or may be triggered at predetermined intervals.

FIG. 1B shows an example in accordance with one or more embodiments where a connection between one of the in-network healthcare facilities and the cloud (101) is disconnected. In this state, the application may automatically configure the local computers (111) and local servers (107) at the disconnected healthcare facility to access the local data stored in the local repository (109). In one or more embodiments, the disconnected healthcare facility continues to store into the local repository (109) medical images and data taken or updated during the time of disconnection. This enables the disconnected healthcare facility to establish a continuous workflow without experiencing any downtime caused by the disconnection from the cloud (101).

Then, when the connection between the disconnected healthcare facility is reestablished with the cloud (101), the local computers (111) and local servers (107) of the reconnected healthcare facility may be configured by the application to transmit to the cloud (101) all of the medical images and data stored in the local repository taken or updated during the time of disconnection. Such medical images and data may then be stored in the cloud repository (105) as new remote data. As the cloud (101) is being updated with the medical images and data from the reconnected healthcare facility, the application stored in the local computers (111) of the other in-network facilities may automatically update their respective local repositories (109) with the new remote data.

FIGS. 2A and 2B show a display message (201) in accordance with one or more embodiments, which may be displayed as part of a pop-up window by the application on the local computer (111) for its user. In this example, the display message (201) includes a user-selectable tab (203a and 203b) (e.g., selectable by the user with a click of a mouse) and a countdown timer (205). The display message (201) may appear as a pop-up window on a display of the local computer (111). The display message (201) may contain a message related to the current connection status between the local servers (107) of the in-network healthcare facilities and the cloud server (103).

FIG. 2A shows an example of the display message (201) when the connection between a local sever (107) of one of the in-network healthcare facilities and the cloud server (103) is disconnected. The display message (201) would include a message that indicates that the connection to the cloud (101) has been disconnected and that the local computer (111) will automatically access the local repository (109) when the countdown timer (205) runs out. Although a single local repository is used in certain descriptions herein for illustration purposes, the number of local computers and local repositories at each healthcare facility may vary.

In one or more embodiments, the users operating the local computer (111) may either wait for the countdown timer (205) to run out or directly click on the user-selectable tab (203a) to access the local repository (109) instead of the cloud repository (105) (i.e., switch access to the local repository (109)).

FIG. 2B shows an example of the display message (201) when the connection between a local sever (107) of one of the disconnected in-network healthcare facility and the cloud server (103) is reestablished. The display message (201) would include a message that indicates that the connection to the cloud (101) has been reestablished and prompts the user (e.g., healthcare professional) to choose between continuing to work off the local repository (109) or to re-access the cloud repository (105). In one or more embodiments, the application of the system (100) gives the user the option to work off the local repository only temporarily (e.g., for a pre-set or predetermined time period). In such a case, as shown in the example of FIG. 2B, the display message (201) may further include a message indicating that the local computer (111) would automatically re-access the cloud repository (105) when the countdown timer (205) runs out (i.e., switch access back to the cloud repository (105)).

Still referring to FIG. 2B, in one or more embodiments, the user may either select user-selectable tab (203a) to immediately re-access the network repository (105) or select user-selectable tab (203b) to continue to work locally off the local repository (109). Again, in this example, the continued use of the local repository after the connection with the cloud has been reestablished is limited. Once the pre-set time period has expired, the user would be prompted with another display message (201) to reconnect to the cloud (101).

FIG. 3 shows an example of a data table (300) that includes data associated with each medical image. In one or more embodiments, the data table (300) may include patient related information such as, but not limited to, a Patient ID (301), Patient Name (303), Attributed Facility ID (305), Report Information (307), and Image Information (309).

In one or more embodiments, the Patient ID (301) is an individual's patient identification number. Each individual will have a single unique Patient ID (301). The individual's Patient ID (301) is shared among the in-network healthcare facilities. The Patient Name (303) is the legal name of the individual.

In one or more embodiments, the Attributed Facility ID (305) may be the identification number of the in-network healthcare facility where the individual is a patient (e.g., the in-network healthcare facility associated with the individual). If an individual frequents more than one of the multiple in-network healthcare facilities, the individual will be associated with more than one Attributed Facility ID (305). Alternatively, in one or more embodiments, the Attributed Facility ID (305) may be the identification number of the in-network healthcare facility that obtained the first image of the particular patient uploaded onto the cloud (101), in which case the patient will have no more than one Attributed Facility ID (305). In one or more embodiments, the Attributed Facility ID may be assigned directly by a user at an in-network healthcare facility (i.e., a healthcare professional).

In one or more embodiments, the Report Information (307) includes information on the individual's medical diagnosis. The Image Information (309) includes a brief description of the medical image and the name of the modality used to generate the medical image.

In one or more embodiments, the data in data table (300) is embedded as metadata in the medical image, which may be a Digital Imaging and Communications in Medicine Format (DICOM-format) image. In one or more embodiments, DICOM may be the universal image format for implementing the system (100). The data from the table (300) can be extracted from the DICOM-format images using the application of one or more embodiments stored in the local computers (111). In one or more embodiments, the data in data table (300) may also be directly imbedded as metadata in the medical data, which can be either the patient's medical images or a patient's medical report.

The data in the table (300) may be sorted in any number of ways. In the example shown FIG. 3, the data is sorted by patient. However, the data can be sorted another way using any one of the patient related information based, for example, on the preferences of the healthcare professionals. Once the data from the data table (300) has been extracted from the medical image, healthcare professionals can edit/modify the data using the GUI provided with the application of one or more embodiments. In one or more embodiments, the extracted data table (300) is stored in the local servers (107).

FIGS. 4-7 show different states of the system of FIGS. 1A and 1B in accordance with one or more embodiments. The cloud (101), the cloud server (103), the cloud repository (105), the local servers (107), the local repository (109), the local computers (111), the display message (201), the user selectable tab(s) (203a and 203b), and the countdown timer (205) may be identical or substantially similar as described above with respect to FIGS. 1A, 1B, 2A, and 2B. Detailed descriptions of such like components will not be repeated below.

Figure 4:
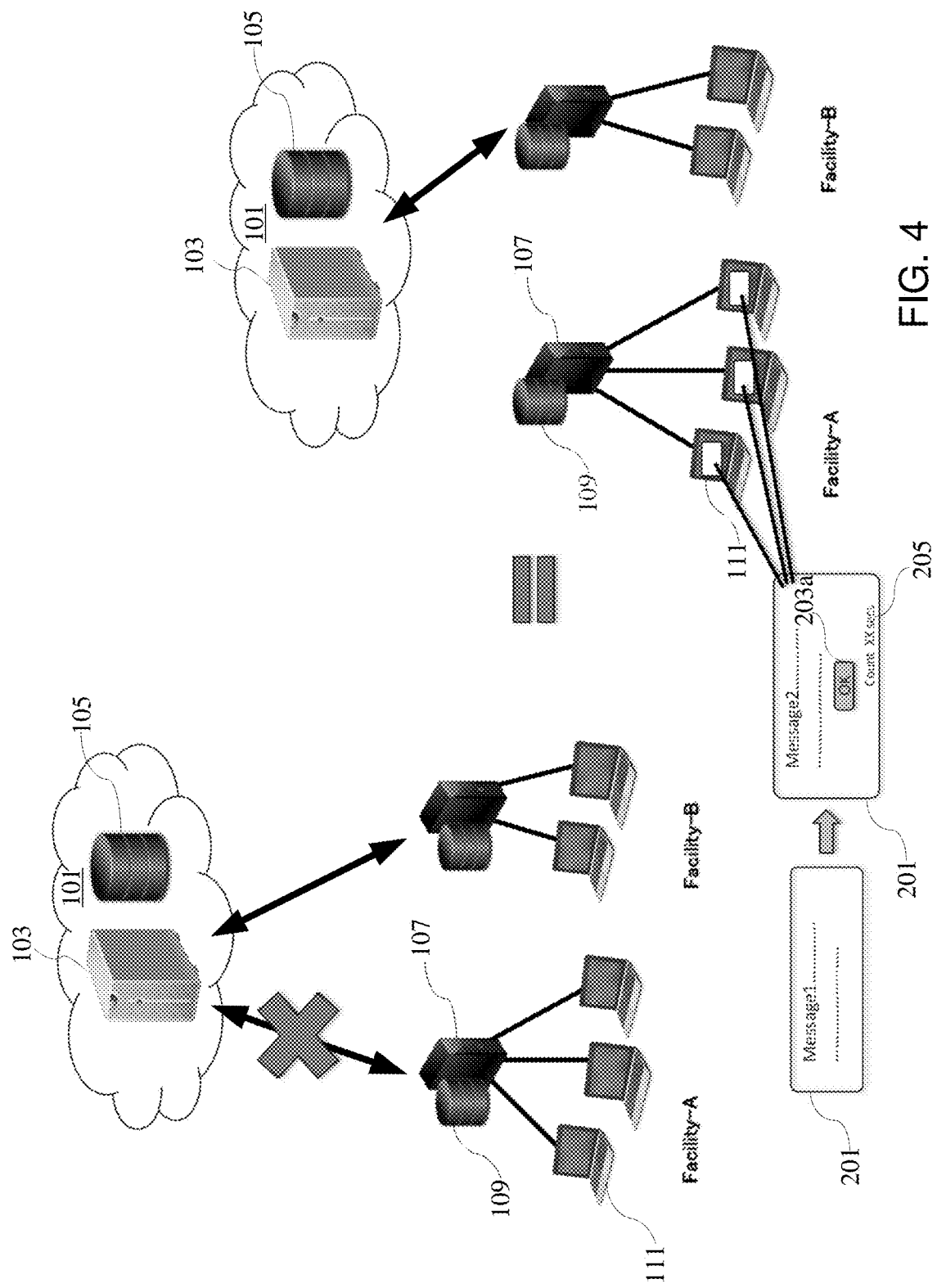
FIG. 4 shows a state of the system of FIGS. 1A and 1B in accordance with one or more embodiments.
Figure 5:
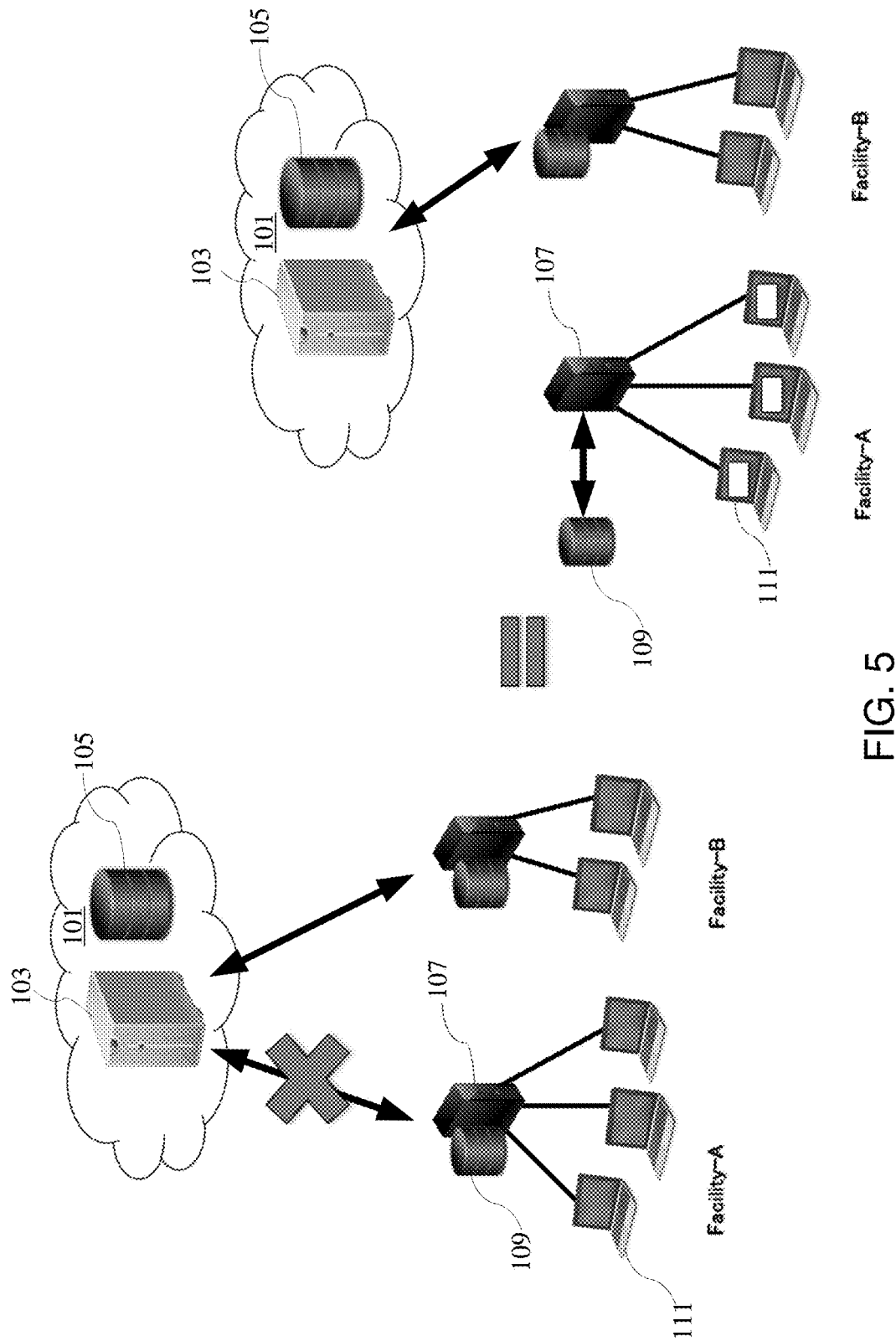
FIG. 5 shows a state of the system of FIGS. 1A and 1B in accordance with one or more embodiments.

FIGS. 4 and 5 each show a state where a connection between a healthcare facility among the multiple in-network healthcare facilities and the cloud (101) gets disconnected. In this case, as shown on the right-hand side of FIG. 4, the local computers (111) associated with the disconnected healthcare facility may first display the display message (201) to indicate that the connection to the cloud (101) is disconnected. The display message (201) may then prompt the user to switch access from the cloud repository (105) to the local repository (109) of the disconnected healthcare facility by selecting the user selectable tab (203a). Additionally or alternatively, the display message (201) may show the user the countdown timer (205) so that the switch will occur automatically once the timer has run out. The right-hand side of FIG. 5 shows the local computers (111) and local servers (107) associated with the disconnected healthcare facility has switched access from the cloud repository (105) to the local repository (109).

Figure 6:
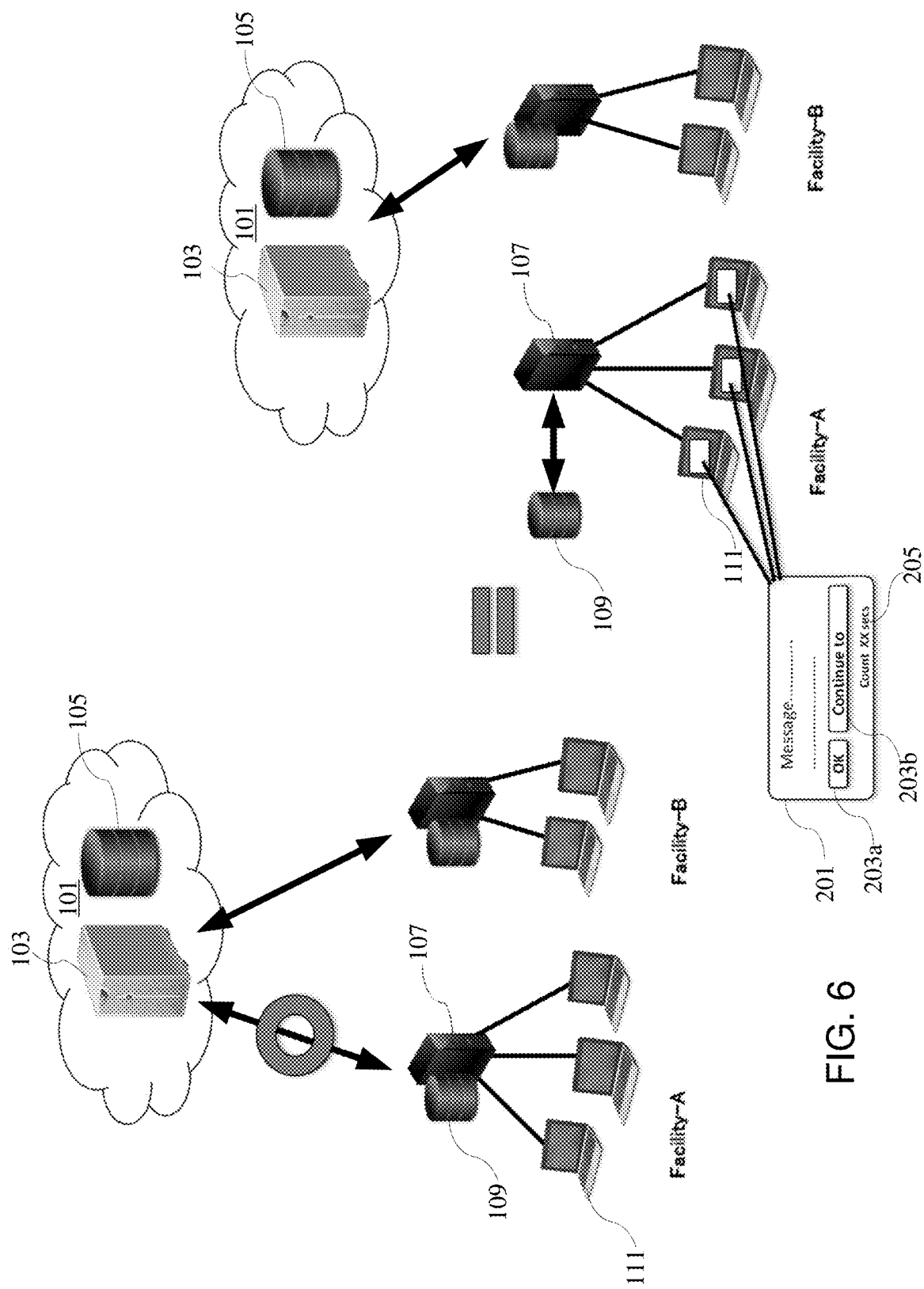
FIG. 6 shows a state of the system of FIGS. 1A and 1B in accordance with one or more embodiments.
Figure 7:
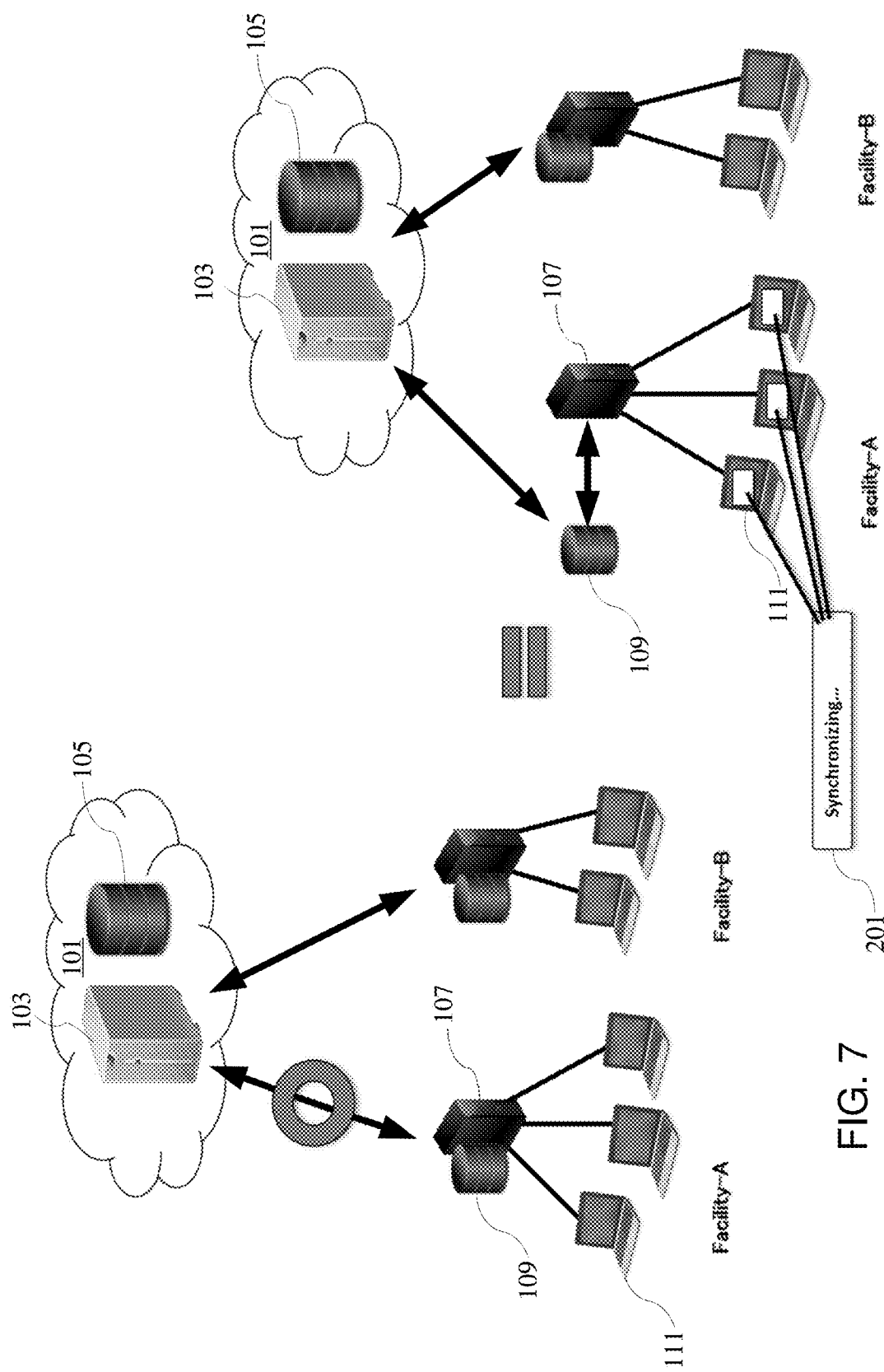
FIG. 7 shows a state of the system of FIGS. 1A and 1B in accordance with one or more embodiments.

FIGS. 6 and 7 each show a state where a connection is reestablished between the disconnected healthcare facility and the cloud (101). In this case, as shown on the right-hand side of FIG. 6, the local computers (111) associated with the re-connected healthcare facility may first display the display message (201) to indicate that the connection to the cloud (101) is re-connected. The display message (201) may then prompt the user to choose between re-accessing the cloud repository (105) (by selecting the user selectable tab (203a)) or continuing to work locally (by selecting the user selectable tab (203b)). Additionally or alternatively, the display message (201) may show the user the countdown timer (205) so that the re-accessing (i.e., switching access from the local repository (109) back to the cloud repository (105))

will occur automatically once the timer has run out. The right-hand side of FIG. 7 shows the local computers (111) associated with the re-connected healthcare facility displaying the display message (201) to indicate that the data stored in the local repository (109) during the time of disconnection is being transmitted to the cloud repository (105), and that the cloud repository (105) is synchronizing with the local repository (109).

In one or more embodiments as discussed in reference to FIGS. 4 and 5, if the disconnected healthcare facility was disconnected during or after a medical synchronization application update process was executed by the cloud-based PACS, the version of the medical synchronization application of the disconnected healthcare facility would not get updated. If the disconnected healthcare facility re-connects to the cloud (101) as discussed in reference to FIGS. 6 and 7, a version mismatch could occur between the medical synchronization application of the re-connected healthcare facility and the cloud (101) if the medical synchronization application of the cloud (101) has finished updating.

FIGS. 8A to 8E show an example of a main GUI (800) in accordance with one or more embodiments, which is displayed to an authorized user on a display of a computing device coupled to the cloud server (103) or any one of the local servers (107). In one or more embodiments, the main GUI (800) may be accessed by the authorized user through the medical synchronization application. In one or more embodiments, the authorized user may be a system administrator who is directly associated with the vendor providing the cloud-based PACS.

Figure 8A:
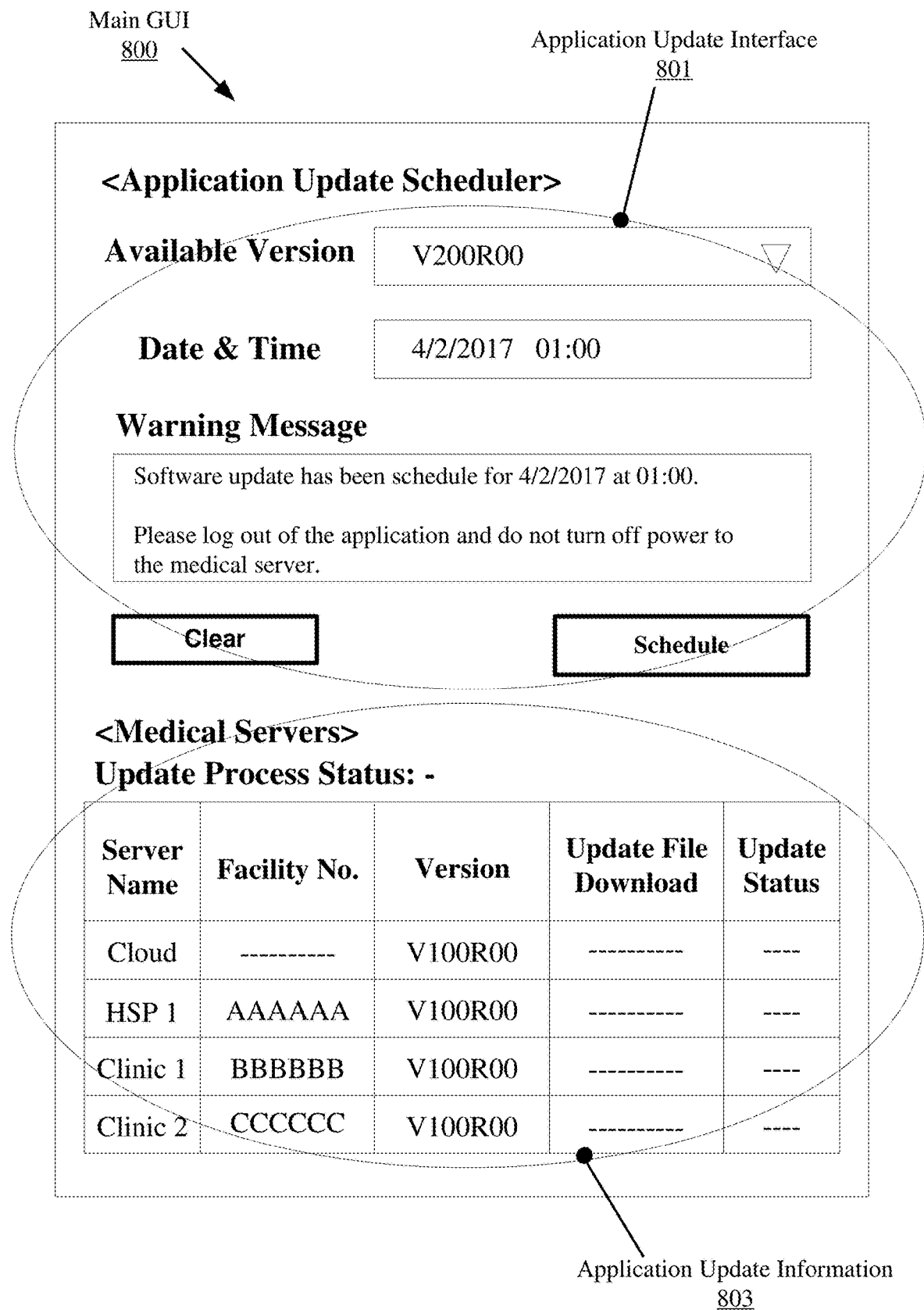
FIGS. 8A to 8E show a user interface in accordance with one or more embodiments.

FIG. 8A shows an initial state of the main GUI (800) for the authorized user to schedule a medical synchronization application update (herein referred to as "synch app update"). In one or more embodiments, the main GUI (800) includes an application update interface (801) and application update information (803). The application update interface (801) includes fields for the user to input or edit update scheduling information such as information on the available version of the medical synchronization application, a date and time for executing an update of the medical synchronization application in all of the devices connected to the cloud-based PACS system, and a user customizable warning message that enables the authorized user to notify (i.e., warn) all of the users at the healthcare facilities that the medical synchronization application update has been scheduled.

In one or more embodiments the application update interface (801) includes a first user-selectable tab that enables the authorized user to clear all of the update scheduling information. The application update interface (801) further includes a second user-selectable tab that enables the authorized user to schedule the synch app update based on the update scheduling information.

In one or more embodiments, the application update information (803) includes a status of the synch app update and a data table that includes information on each of the devices connected to the cloud-based PACS system.

In one or more embodiments, the data table of the application update information (803) includes information such as the name of each server ("Server Name") within the cloud-based PACS system, an identification number for each healthcare facility ("Facility No."), a version of the medical synchronization application ("Version"), status of the update file download to each server ("Update File Download"), and status of the update for each server ("Update Status"). The information in the data table of the application update information (803) may be updated throughout the synch app update to present a real-time status of the synch app update to the authorized user.

Figure 8B:
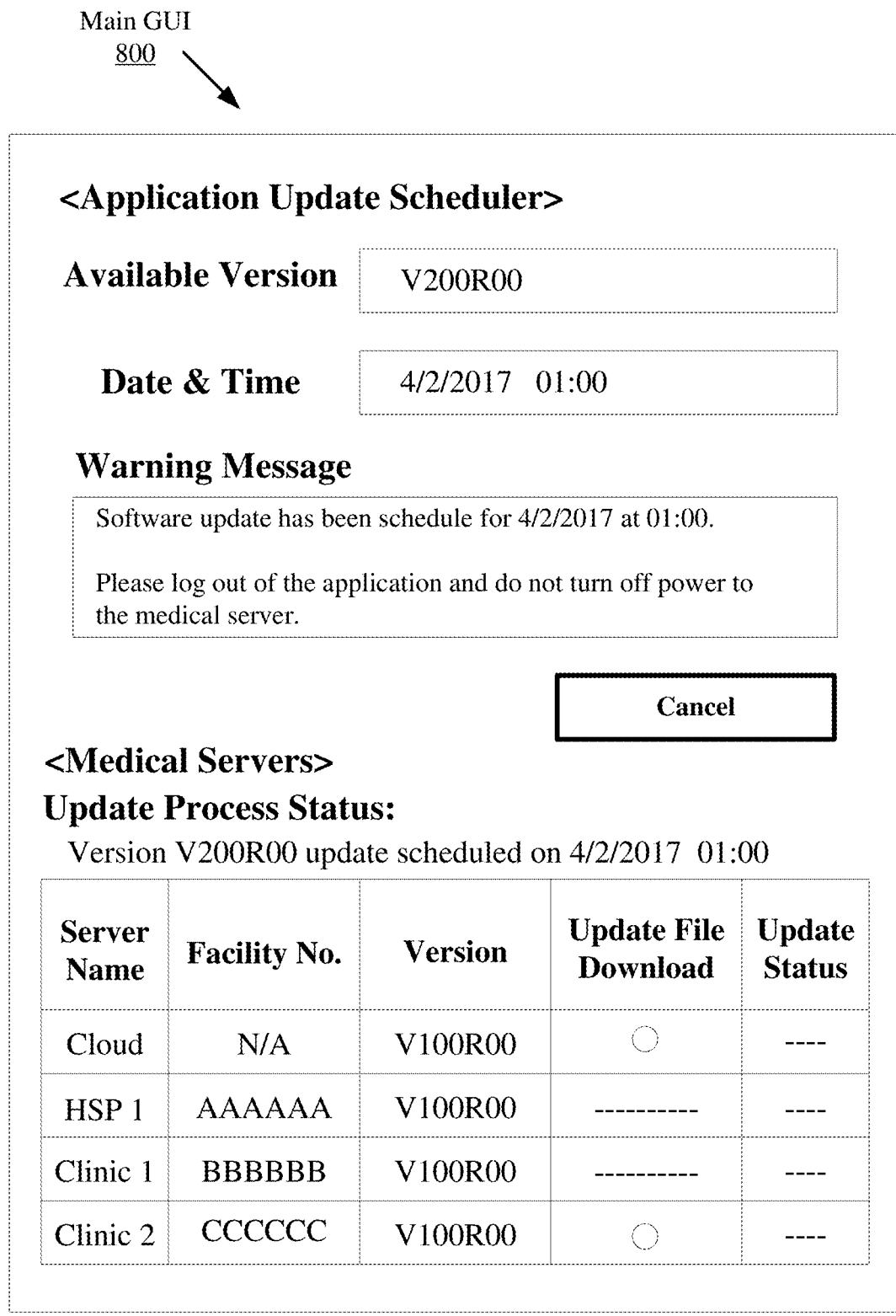

FIG. 8B shows a state of the main GUI (800) after the authorized user has confirmed the update scheduling information and selected the second user-selectable tab to schedule the synch app update. In one or more embodiments, the status of the synch app update in the application update information (803) is changed to reflect the update scheduling information. The authorized user may still cancel the synch app update before the date and time for executing the synch app update is reached.

In one or more embodiments, once the synch app update has been scheduled, the cloud server (103) will transmit an instruction to each local server (107) connected to the cloud (101) that includes the update file for updating the medical synchronization application. Once a local server (107) has received the update file, the Update File Download information for that local server (107) will be updated to indicate that the update file has been successfully received (i.e., downloaded) by the local server (107).

Figure 8C:
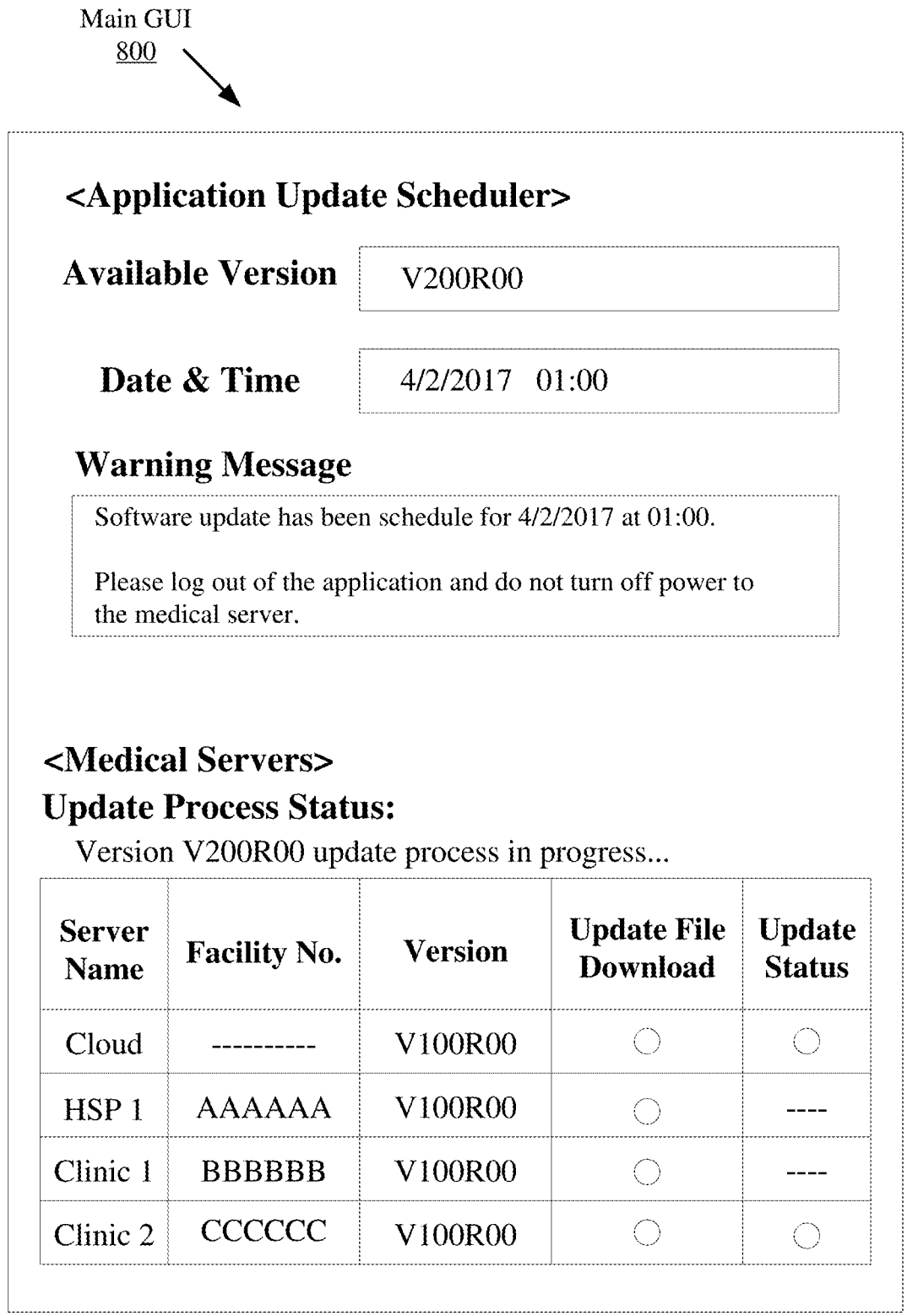

FIG. 8C shows a state of the main GUI (800) after the date and time for executing the synch app update have been reached. In one or more embodiments, once the synch app update has been executed, the synch app update cannot be cancelled. The status of the synch app update of the application update information (803) is updated to reflect that the synch app update has been executed.

Figure 8D:
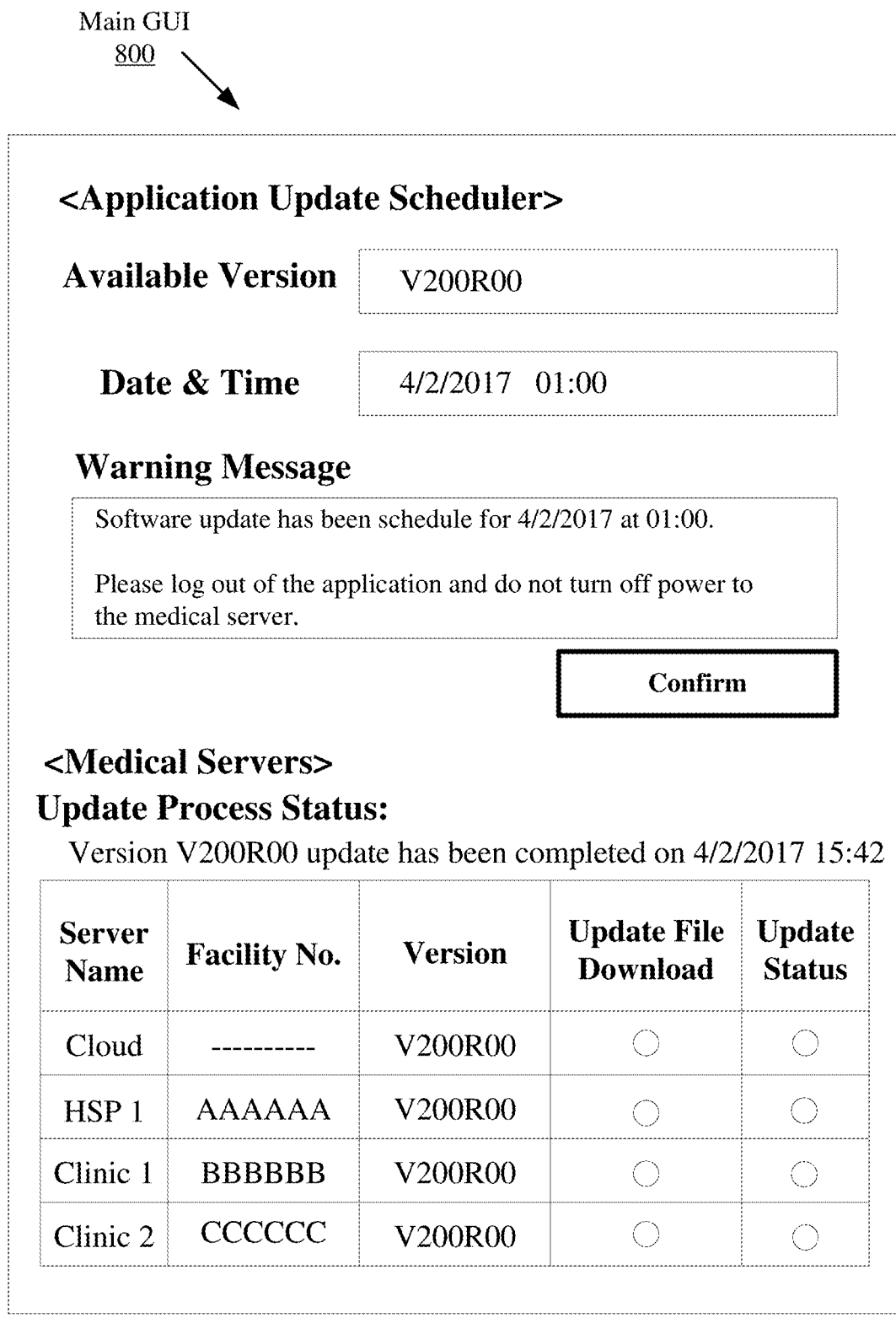

FIG. 8D shows a state of the main GUI (800) after the synch app update has been completed. In one or more embodiments, the status of the synch app update and the information in the data table of the application update information (803) are updated to reflect that the synch app update has been completed. A third user-selectable tab is provided in the application update interface (801) for the authorized user to confirm that the synch app update is complete.

Figure 8E:

FIG. 8E shows a state of the main GUI (800) after the authorized user selected the third user-selectable tab to confirm that the synch app update is complete. In one or more embodiments, the state of the main GUI (800) returns to that as described in FIG. 8A for the authorized user to schedule the next synch app update.

Figure 9A:
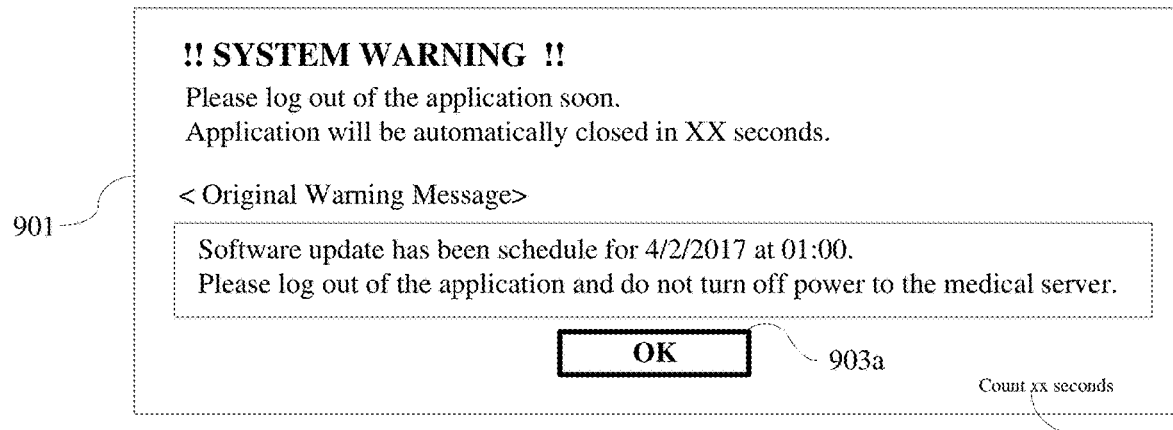
FIGS. 9A and 9B show a display message in accordance with one or more embodiments.
Figure 9B:
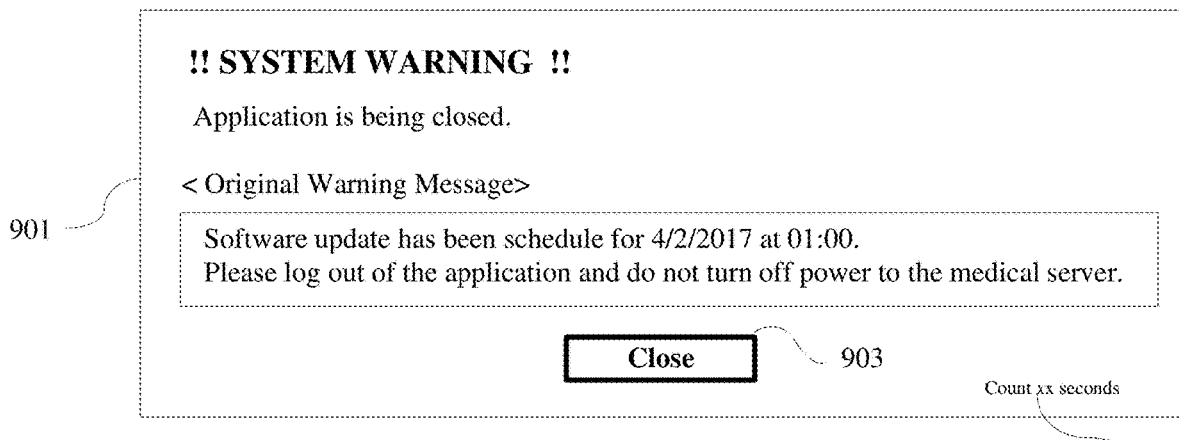

FIGS. 9A and 9B show a display message (901) in accordance with one or more embodiments, which may be displayed as part of a pop-up window by the application on the local computer (111) for its user. In this example, the display message (901) includes a user-selectable tab (903) (e.g., selectable by the user with a click of a mouse) and a countdown timer (905). The display message (901) may appear as a pop-up window on a display of the local computer (111). The display message (901) may contain a warning message that an authorized user on the vendor end has scheduled a synch app update.

FIG. 9A shows an example of the display message (901) when the local server (107) coupled to the local computer (111) received an instruction from the cloud server (103) to update the medical synchronization application. The display message (901) includes the warning message input by the authorized user into the main GUI (800) as shown in FIG. 8A. The display further includes a different warning message that instructs the user of the local computer (111) to log-out of the medical synchronization application and indicates that the synchronization will automatically be closed when a countdown timer (905) runs out.

In one or more embodiments, the user of the local computer (111) may wait for the medical synchronization application to automatically close out when countdown timer (905) runs out. Alternatively, the user may close the display message (901) to save any current progress by clicking on the user-selectable tab (903*a*) and then manually close medical synchronization application.

FIG. 9B shows an example of the display message (901) after a predetermined time has passed after the user has closed the display message (901) as shown in FIG. 9A but has not closed the medical synchronization application. The display message (901) includes the warning message input by the authorized user into the main GUI (800) as shown in FIG. 8A and a different message indicating that the medical synchronization application is being forcefully closed by the local computer (111).

In one or more embodiments, the display message (901) as shown in FIG. 9B may be displayed to the user approximately 30 seconds before the countdown timer (905) runs out.

In one or more embodiments, the user of the local computer (111) may either wait for the medical synchronization application to automatically close out when countdown timer (905) runs out. Alternatively, the user may close the display message (901) to immediately close the medical synchronization application by clicking on the user-selectable tab (903*a*).

Figure 10:
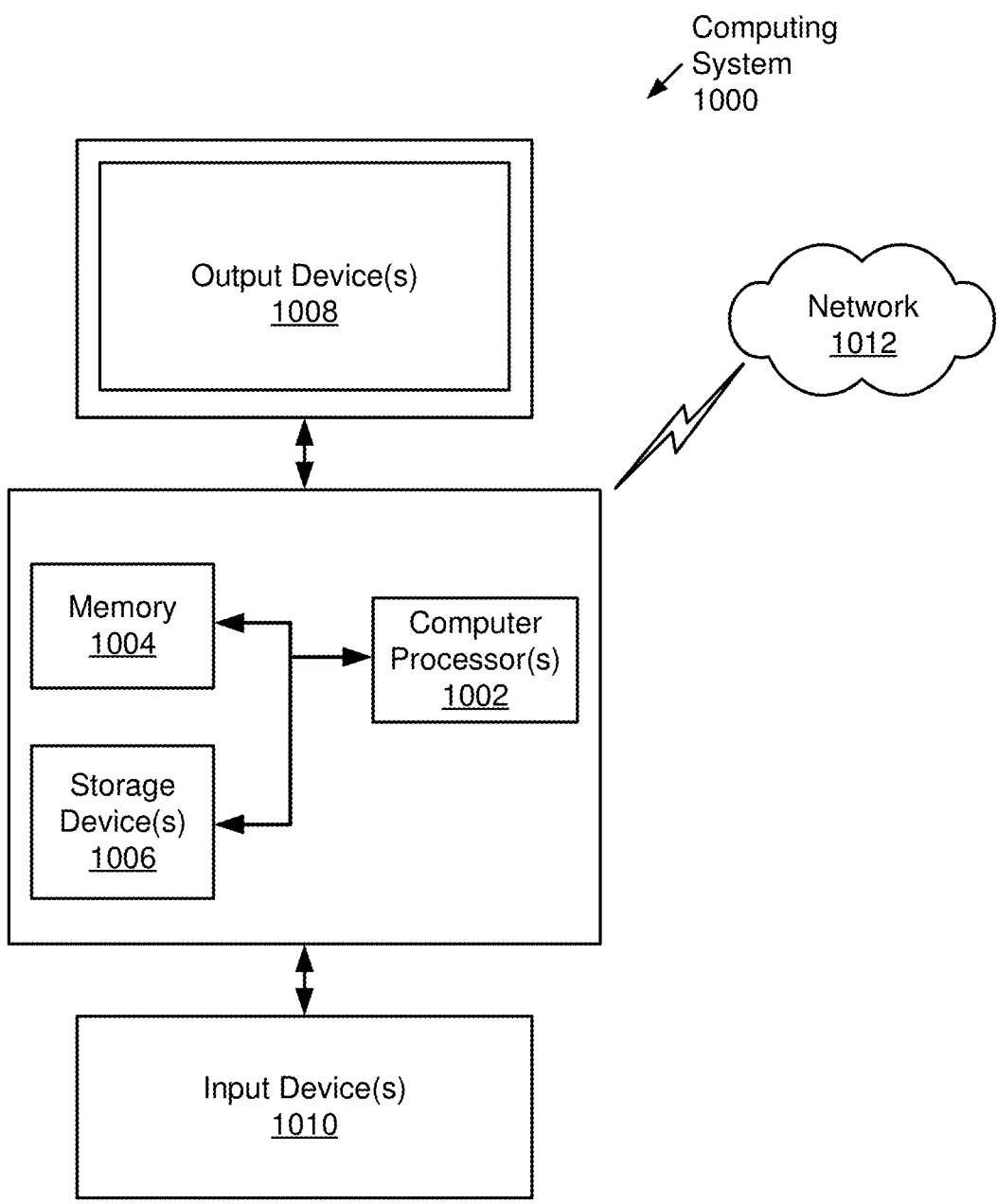
FIG. 10 shows a computing system in accordance with one or more embodiments.

Embodiments of the invention may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention. For example, as shown in FIG. 10, the computing system (1000) may include one or more computer processor(s) (1002), associated memory (1004) (e.g., random access memory (RAM), cache memory, flash memory, etc.), one or more storage device(s) (1006) (e.g., a hard disk, an optical drive such as a compact disk (CD) drive or digital versatile disk (DVD) drive, a flash memory stick, etc.), and numerous other elements and functionalities. The computer processor(s) (1002) may be an integrated circuit for processing instructions. For example, the computer processor(s) may be one or more cores, or micro-cores of a processor. The computing system (1000) may also include one or more input device(s) (1010), such as a touchscreen, keyboard, mouse, microphone, touchpad, electronic pen, or any other type of input device. Further, the computing system (1000) may include one or more output device(s) (1008), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (1000) may be connected to a network (1012) (e.g., a local area network (LAN), a wide area network (WAN) such as the Internet, mobile network, or any other type of network) via a network interface connection (not shown). The input and output device(s) may be locally or remotely (e.g., via the network (1012)) connected to the computer processor(s) (1002), memory (1004), and storage device(s) (1006). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (1000) may be located at a remote location and connected to the other elements over a network (1012). Further, one or more embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

The computing system of FIG. 10 may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Figure 11:
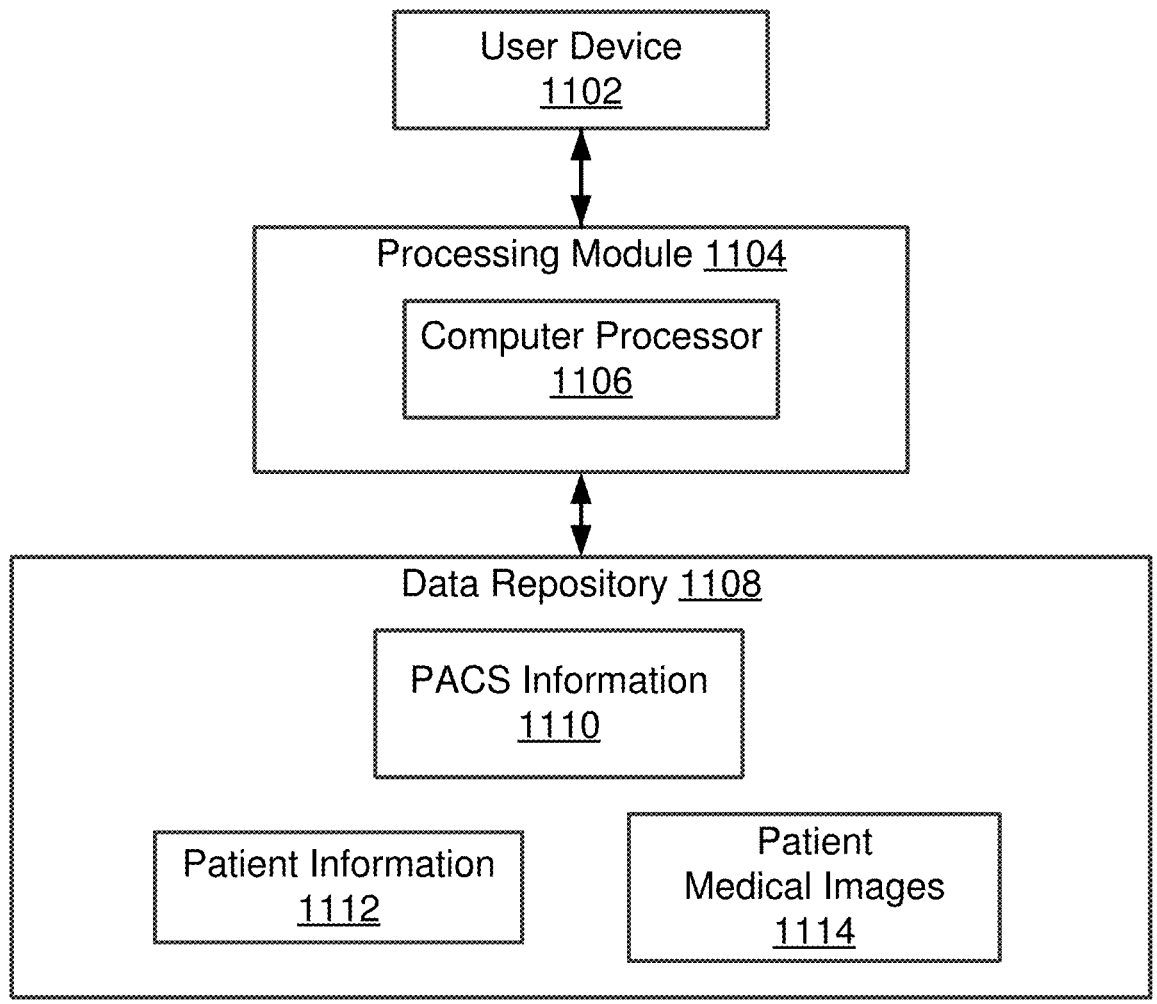
FIG. 11 shows a schematic diagram in accordance with one or more embodiments.

FIG. 11 shows a schematic diagram of a system in accordance with one or more embodiments. The system is configured for synchronizing medical images and data between a cloud repository on a cloud server and a plurality of local repositories on a plurality of local servers connected to the cloud server. The plurality of local servers includes a first local server and the plurality of local repositories includes a first local repository on the first local server. As explained above, the use of ordinal numbers does not imply or create a particular ordering of the elements or limit any element to being only a single element. For example, the "first local server" may be any local server among the plurality of local servers connected to the cloud server, and is merely called "first" for purposes of illustration.

The system as shown in FIG. 11 may include, for example, (i) a processing module (1104) including a computer processor (1106) configured to execute instructions configured to perform the following steps based on the connection status between the first local server and the cloud server.

In one aspect, the computer processor (1106) executes instructions to cause the cloud server to (1) receive a request to update a medical synchronization application stored on the cloud server and each of the local servers using an update file, (2) transmit, to each of the local servers, an instruction to update the medical synchronization application, wherein the instruction includes the update file, (3) determine, a version information of the medical synchronization application on all of the local servers, and (4) execute the update file to update the medical synchronization application on the cloud server only in the event that cloud server determines that the medical synchronization application of all of the local servers have been updated, and In yet another aspect, in response to one of the plurality of local servers establishing a connection with the cloud server, the computer processor (1106) causes the cloud server to (1) determine the version information of the medical synchronization application of the local server establishing the connection, and (2) in the event that the version information of the medical synchronization application of the local server establishing the connection is different from the version information of the medical synchronization application on the cloud server, transmit the instruction to update the medical synchronization application to the local server establishing the connection.

The system as shown in FIG. 11 further comprises (ii) a user device (1102) configured to present the medical images and data to a user. The system may further include a data repository (1108) configured to store PACS application data (i.e., PACS information) (1110) related to the vendor provided application, the patient information (1112), and the medical images and data (1114).

Figure 12A:
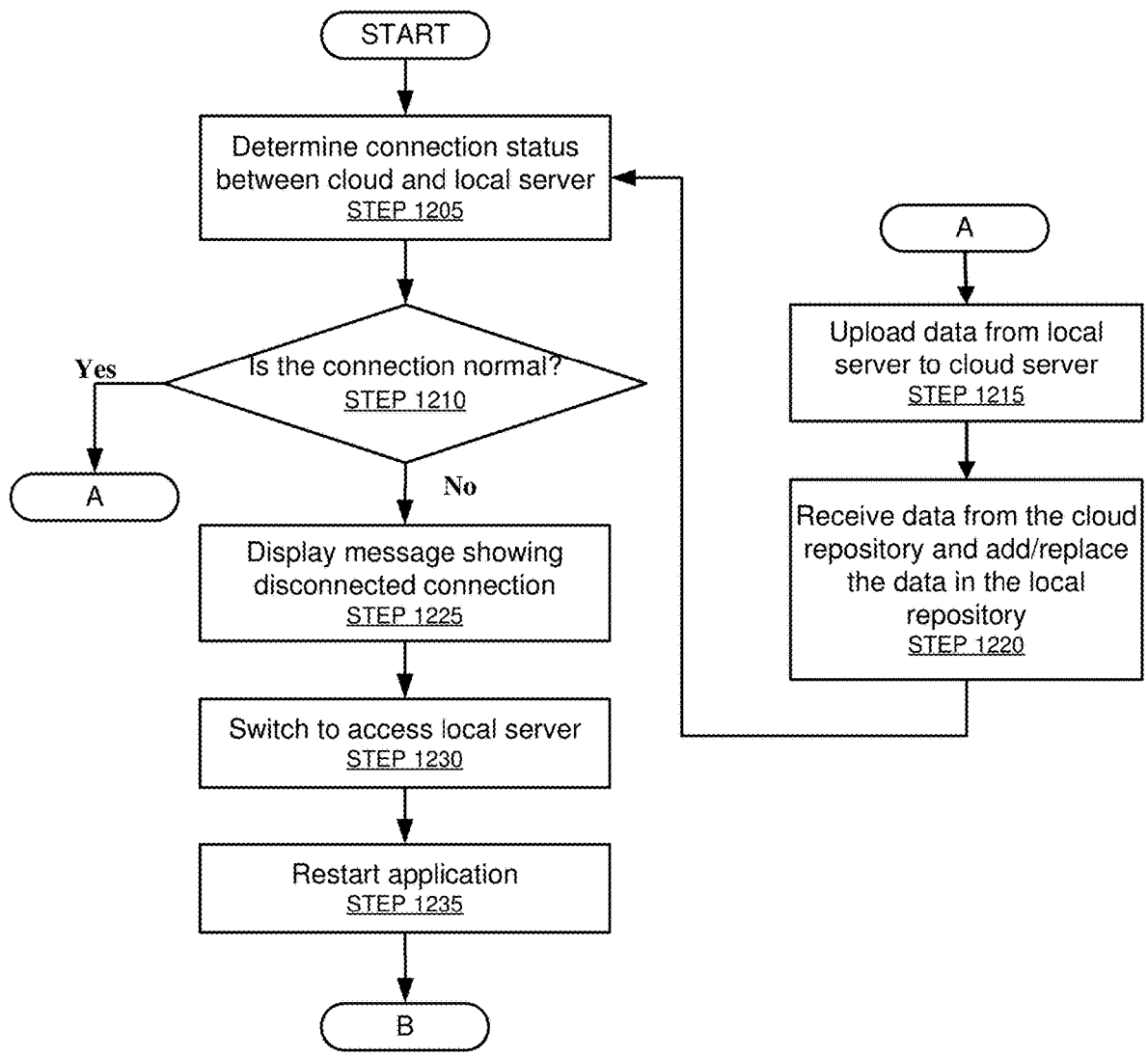
FIGS. 12A and 12B show a flowchart in accordance with one or more embodiments.
Figure 12B:
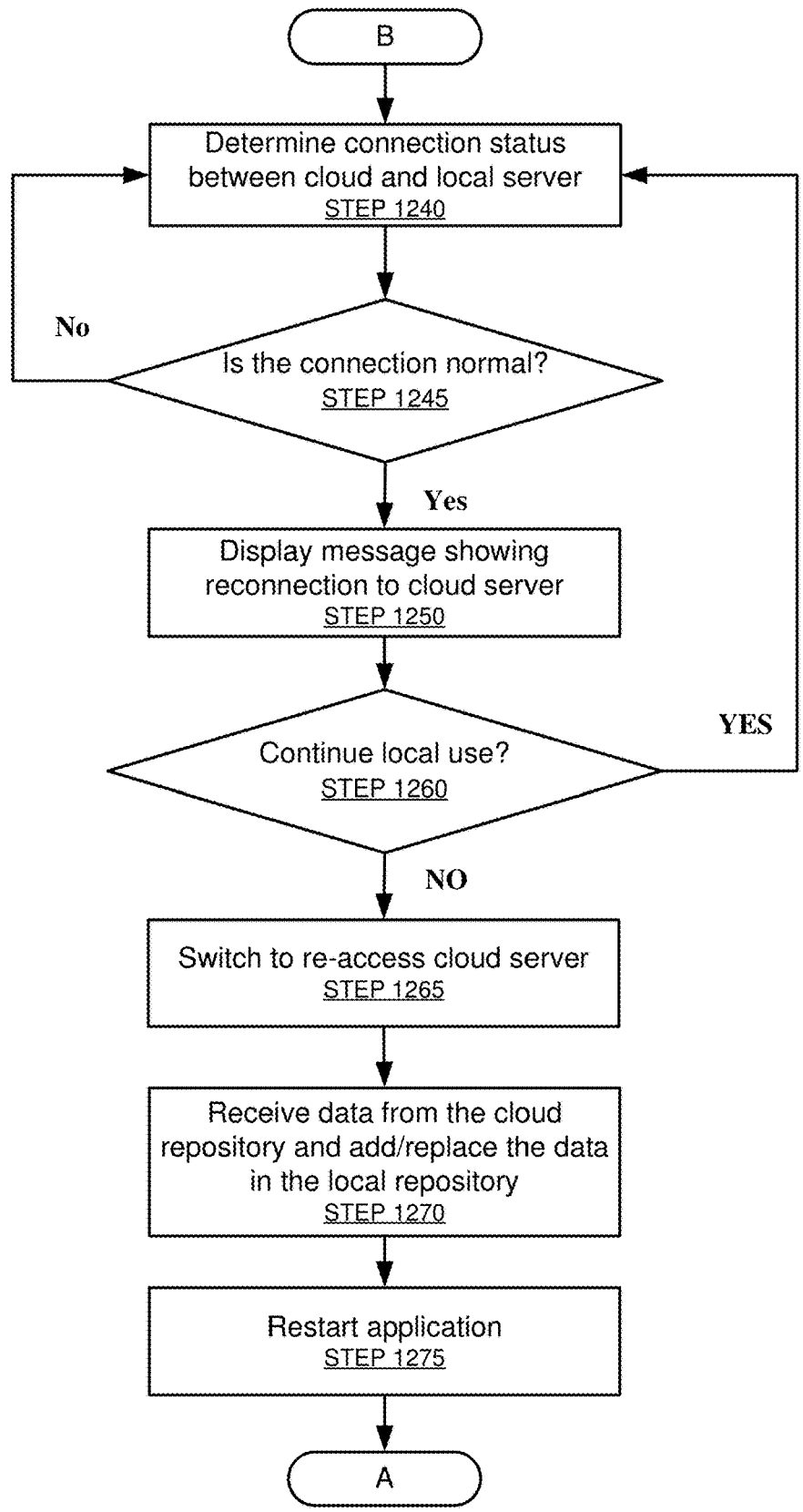

FIGS. 12A and 12B show a flowchart of a method in accordance with one or more embodiments. In one or more embodiments, the method as shown in FIGS. 12A and 12B is a computer-implemented method. Each step shown in FIGS. 12A and 12B are described together below with respect to only a system of one healthcare facility among the multiple in-network healthcare facilities. It would be apparent to one of ordinary skill in the art that each step of the method described below can be performed by any of the systems of the multiple in-network healthcare facilities.

In Steps 1205 and 1210, the local computers associated with one of the in-network healthcare facilities check the status of the connection between the local servers of the healthcare facility and the cloud server on the cloud to determine if the connection is normal.

If the result of the check in Step 1210 is YES, the local computers continue to upload data generated by the modalities to the cloud server through the local servers in Step 1215, and synchronize a data between the local repositories and the cloud repository in Step 1220. The process then returns to Step 1205.

In one more embodiments, in response to the cloud server being updated in Step 1215, the local computers and servers of the other in-network facilities will receive either all or part of the updated data from the cloud server. When the local computers and servers of the in-network facilities receive the updated data, the respective local computers and servers will either add the updated data to the respective local repositories if the updated data did not previously exist, or replace pre-existing locally-stored data that corresponds to the updated data with the updated data.

If the result of the check in Step 1210 is NO, a message is displayed in Step 1225 to the user indicating that the connection between the healthcare facility and the cloud is disconnected, and that the local computers and servers will be switching access to the local repository (or repositories).

In Step 1230, the local computers and servers of the disconnected healthcare facility switch access to the local repository, and, in Step 1235, an application stored on the local computers and servers that enable the local computers and servers to access the cloud is restarted. At this point, the medical images and data are being stored and retrieved from the local repository instead of from the cloud repository.

In one or more embodiments, when the message is displayed to the users, the users can either click on a user-selectable tab to instantly switch access to the local repository or wait for the local computers and servers to automatically switch access to the local repository when a countdown timer displayed on the message to run out.

In Steps 1240 and 1245, once the application has been restarted, the local computers of the disconnected healthcare facilities perform a check to determine if there is a normal connection between the local servers and the cloud server.

If the result of the check is NO, the local computers and servers continue to operate locally and the process returns to Steps 1240 and 1245 where the local computers check the status of the connection between the local server and the cloud server.

If the result of the check is YES, a message is displayed in Step 1250 to the users indicating that the connection between the healthcare facility and the cloud has been reestablished, and that the local computers and servers are switching access back to the remote repository.

In Step 1260, when the message is displayed to the users, the users are prompted to make a determination if the users want to continue to work locally off the local repository. The local computers and servers will automatically re-access the cloud server if a response by the users is not detected by the time a countdown timer on the message runs out.

If the result of the check is YES, the local computers and servers remain on the local connection for a pre-set period where the local computer continues to check the connection status between the local servers and the cloud server in Step 1240. Once the pre-set time period has expired, the user would be prompted with another display message to reconnect to the cloud. This time, the user would not be able to choose to continue to work locally off the local repository.

If the result of the check is NO, the local computers and servers are configured to re-access the cloud repository in Step 1265.

Then, in Step 1270, when the local computers and servers have re-accessed the cloud repository, the cloud repository is synchronized, i.e., updated with data stored in the local repository during the time of reconnection along with new data that was generated after the reconnection with the cloud server. In the event a conflict has occurred during the disconnection (e.g., when more than one user at different in-network healthcare facilities attempts to simultaneously update the patient information associated with the same remote data on the remote server), the conflict may be resolved automatically by the application or manually by the user through a GUI provided by the application.

In one or more embodiments, a conflict may occur when local data from the local servers of the in-network healthcare facilities are being uploaded to the cloud server (e.g., during medical data synchronization between the respective local servers and the cloud server). The conflict may occur when different users at different in-network healthcare facilities attempt to simultaneously update the same portion of the patient information of the same remote data by editing or updating the information locally in the corresponding local data. This may prevent the application from determining which of the updated patient information is correct when the cloud server tries to update the remote data using the information from the two received edited local data.

More specifically, in one or more embodiments, certain conflict situations may be more complex than others. For example, if a user at in-network healthcare facility A updates a patient name from "AAAAA" to "AAABA" and a user at a different in-network healthcare facility updates the same patient name from "AAAAA" to "AAACA," when the two users attempt to simultaneously update the same remote data to reflect the new patient name, the system will be unable to determine which of the two new names is correct. In this case, the user must manually resolve the conflict. However, if the user at in-network health care facility A edits a patient name from "AAAAA," to "AAABA," and a user at in-network healthcare facility B edits the same patient name from "AAAAA," to "ACAAA," then, when the two users attempt to simultaneously update the same remote data to reflect the new patient name, the application will be able to automatically update the patient name to "ACABA."

Further, the local computers and servers of the disconnected healthcare facility will receive data from the cloud server updated by the other in-network healthcare facilities during the time of disconnection and either add the updated data to the local repository if the updated data did not previously exist, or replace pre-existing locally-stored data that corresponds to the updated data with the updated data.

In one or more embodiments, in response to the cloud server being updated in Step 1270, the local computers and servers of the other in-network facilities will receive either all or part of the updated data from the cloud server. When the local computers and servers of the in-network facilities receive the updated data, the respective local computers and servers will either add the updated data to the respective local repositories if the updated data did not previously exist, or replace pre-existing locally-stored data that corresponds to the updated data with the updated data.

In Step 1275, when all of the data stored in the local repository during the time of reconnection is transmitted to the cloud repository, the application is restarted and local computers are configured to return to Step 1205.

FIGS. 13A, 13B, and 13C show an implementation example in accordance with one or more embodiments. As shown in FIGS. 13A, 13B, and 13C each of the functional items is broken down into a large item ("a top-level function") and multiple small items ("sub-functions of the top-level functions"). The top-level functions and the sub-functions are implemented by a user or a respective component of the system shown in FIGS. 1A and 1B during each step of the flowchart as shown in FIGS. 12A, 12B.

According to one or more embodiments, the contents of each sub-function describe the actions that can be implemented by the user or the respective components of the system shown in FIGS. 1A and 1B when each sub-function is being implemented. The actions also show the actions that cannot be implemented by the user when a specific sub-function is being implemented.

According to one or more embodiments, the settings describe a user-set interval or amount of time associated with specific sub-functions that may be repeated or set with a specific time restriction when implemented. The settings may be non-configurable settings that are pre-set by the vendor that provides the application. Further, the settings may be user-configurable settings that can be configured by a user with high administrative authority in the healthcare facility.

Figure 14:
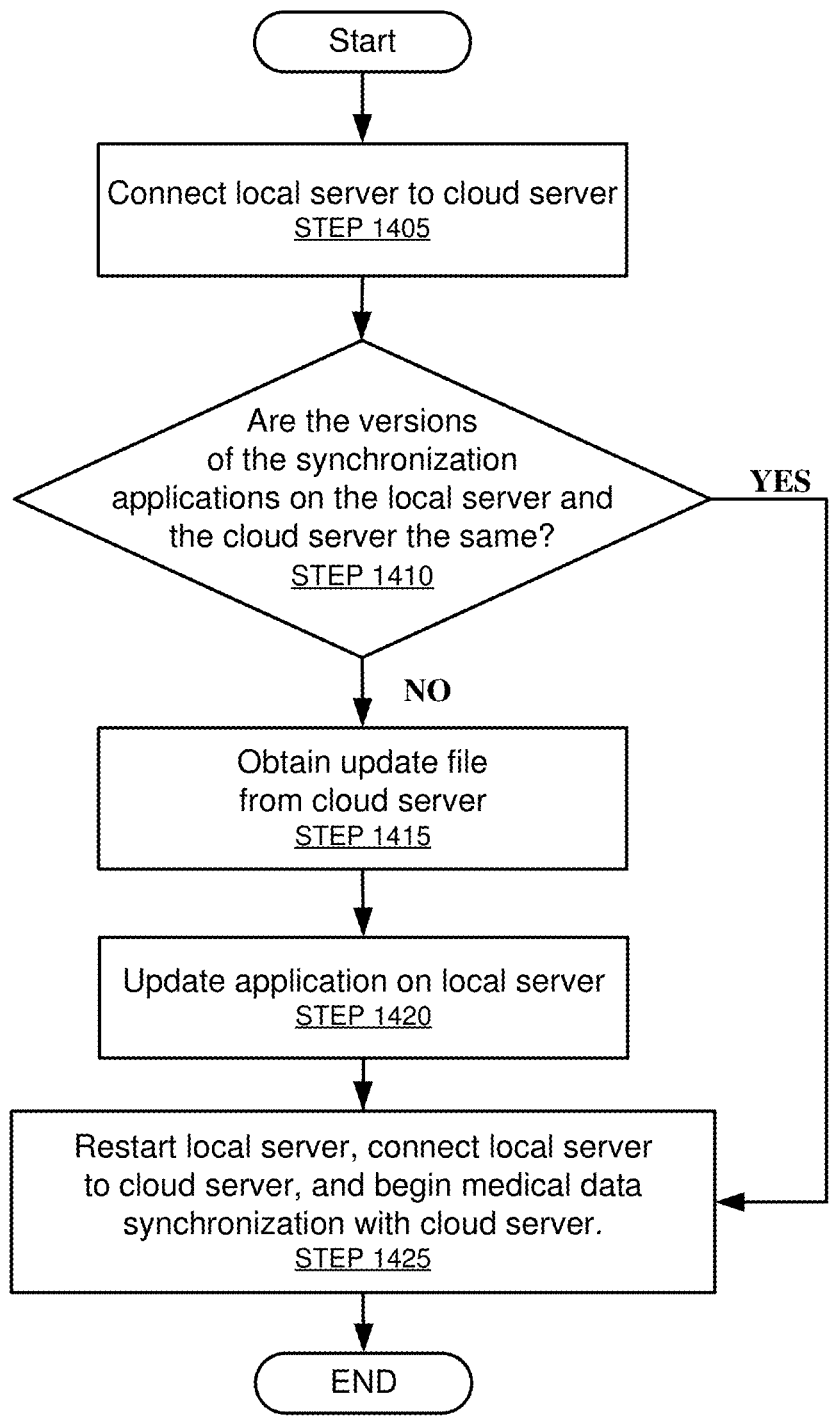
FIG. 14 shows a flowchart in accordance with one or more embodiments.

FIG. 14 shows a flowchart in accordance with one or more embodiments. The method as shown in FIG. 14 may be a computer-implemented method. Each step shown in FIG. 14 is described together below with respect to only a system of one healthcare facility among the multiple in-network healthcare facilities. It would be apparent to one of ordinary skill in the art that each step of the method described below can be performed by any of the systems of the multiple in-network healthcare facilities.

In Step 1405, a local server associated with one of the in-network healthcare facilities is connected to the cloud server on the cloud. In one or more embodiments, the local server may be connecting to the cloud server for the first time. Alternatively, the local server may be re-connecting to the cloud server after being disconnected from the cloud server. In one or more embodiments, the local server is restarted before re-connecting to the cloud server.

In Step 1410, upon connection of the local server with the cloud server, the cloud server determines whether the version information of the medical synchronization application installed on the local server is the same as the version information of the medical synchronization application installed on the cloud server. This enables the cloud server to make sure that the version information of both medical synchronization applications is the same.

In one or more embodiments, if the version information of the medical synchronization applications of the cloud server and local server are different, a synchronization of medical images and data between the cloud server and local server is prohibited. This not only ensures that the connected devices will be applying the same synchronization settings but also ensures that the medical images and data synchronized between the connected devices are accurate and consistent.

If the determination in Step 1410 is NO, the cloud server transmits an instruction to the local server to update the medical synchronization application on the local server. Upon receipt of the instructions, the local server obtains an update file from the cloud server in Step 1415.

In one or more embodiments, the update file is pre-stored in the cloud server by the authorized user or the vendor of the cloud-based PACS before the authorized user schedules an update of the medical synchronization application.

In one or more embodiments, the instruction transmitted from the cloud server includes the update file for updating the medical synchronization application on the local server to the same version as the medical synchronization application on the cloud server. Alternatively, the instruction transmitted by the cloud server includes an instruction for the local server to download the update file from the cloud server.

In Step 1420, the local server executes the update file to update the medical synchronization application on the local server.

In Step 1425, the local server is restarted and re-connected to the cloud server, and a synchronization of medical images and data between the local server and the cloud server is initiated.

If the determination in Step 1410 is YES, the local server connects to the cloud server and begins synchronization of medical images and data with the cloud server.

Figure 15:
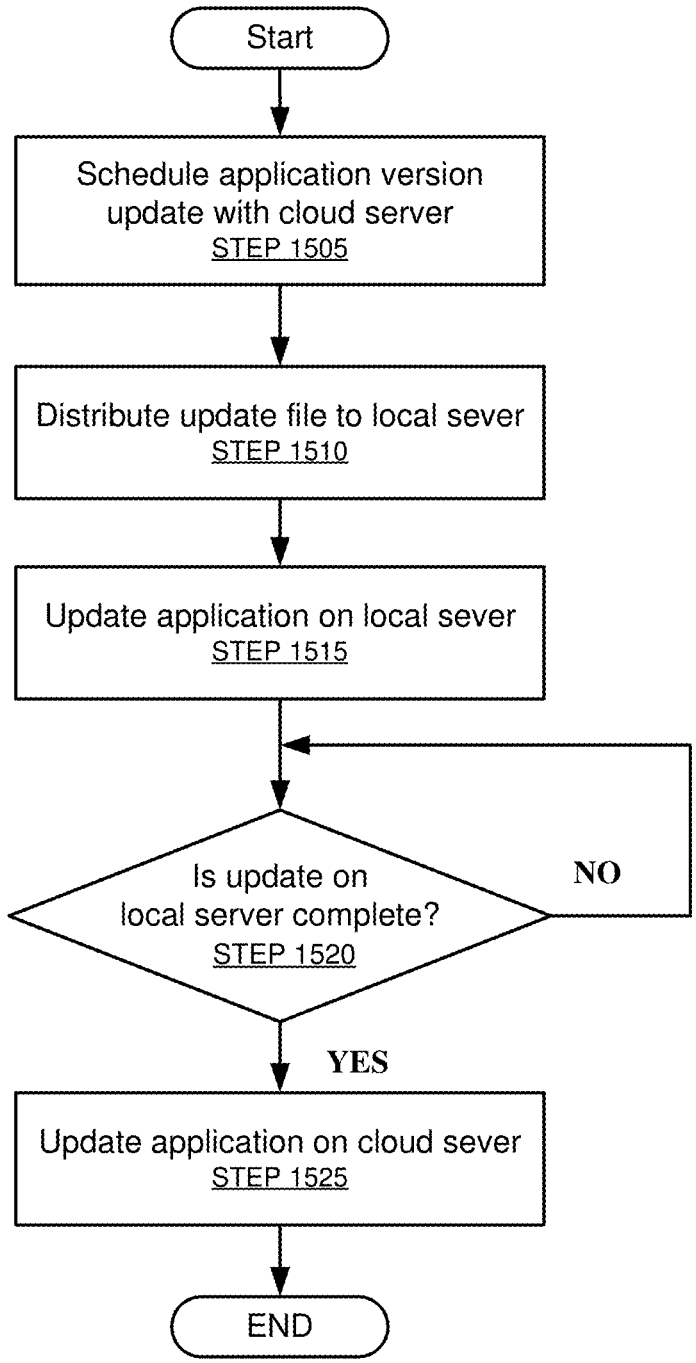
FIG. 15 shows a flowchart in accordance with one or more embodiments.

FIG. 15 shows a flowchart in accordance with one or more embodiments. In one or more embodiments, the method as shown in FIG. 15 is a computer-implemented method.

In Step 1505, the cloud server receives a request to schedule an update for the medical synchronization application stored on the cloud server and each of the local servers connected to the cloud server.

In one or more embodiments, the request can be transmitted to the cloud server by any computing device connected to the cloud server. In one or more embodiments, the update of the medical synchronization application can only be scheduled by an authorized user associated with the vendor of the cloud-based PACS.

In Step 1510, the cloud server transmits an instruction to the local server to update the medical synchronization application on the local server. Upon receipt of the instructions, the local server obtains an update file from the cloud server.

In one or more embodiments, the update file is pre-stored in the cloud server by the authorized user or the vendor of the cloud-based PACS before the authorized user schedules an update of the medical synchronization application.

In one or more embodiments, the instruction transmitted from the cloud server includes the update file for updating the medical synchronization application on the local server to the same version as the medical synchronization application on the cloud server. Alternatively, the instruction transmitted by the cloud server includes an instruction for the local server to download the update file from the cloud server.

In Step 1515, the local server executes the update file to update the medical synchronization application on the local server.

In Step 1520, the cloud server determines whether all of the medical synchronization applications on the local servers are successfully updated.

If the determination in Step 1520 is NO, the cloud waits for all of the local servers to update the medical synchronization application and repeats the determination in Step 1520 after a predetermined amount of time has passed. In one or more embodiments, the predetermined amount of time can be any value that is pre-programmed into the settings of the cloud server by an authorized user associated with the vendor of the cloud-based PACS.

If the determination in Step 1520 is YES, the cloud server executes the update file in Step 1250 to update the medical synchronization application. In one or more embodiments, the cloud server only executes the update file once all of the local servers have completed the update of the respective medical synchronization applications.

Figure 16:
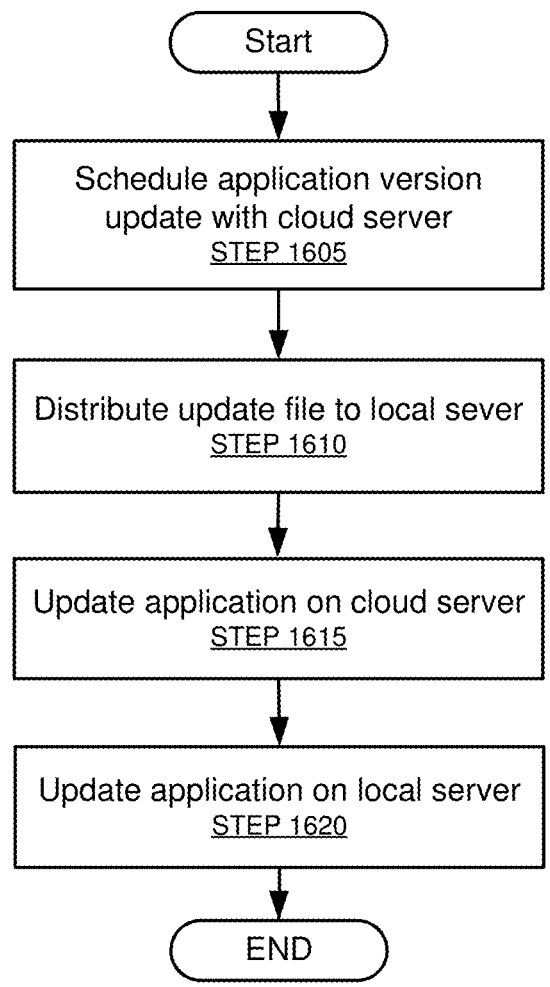
FIG. 16 shows a flowchart in accordance with one or more embodiments.

FIG. 16 shows a flowchart in accordance with one or more embodiments. In one or more embodiments, the method as shown in FIG. 16 is a computer-implemented method.

In Step 1605, the cloud server receives a request to schedule an update for the medical synchronization application stored on the cloud server and each of the local servers connected to the cloud server.

In one or more embodiments, the request can be transmitted to the cloud server by any computing device connected to the cloud server. In one or more embodiments, the update of the medical synchronization application can only be scheduled by an authorized user associated with the vendor of the cloud-based PACS.

In Step 1610, the cloud server transmits an instruction to the local server to update the medical synchronization application on the local server. Upon receipt of the instructions, the local server obtains an update file from the cloud server.

In one or more embodiments, the update file is pre-stored in the cloud server by the authorized user or the vendor of the cloud-based PACS before the authorized user schedules an update of the medical synchronization application.

In one or more embodiments, the instruction transmitted from the cloud server includes the update file for updating the medical synchronization application on the local server to the same version as the medical synchronization application on the cloud server. Alternatively, the instruction transmitted by the cloud server includes an instruction for the local server to download the update file from the cloud server.

In Step 1615, the cloud server executes the update file to update the medical synchronization application.

In Step 1620, the local servers execute the update file to update the respective medical synchronization applications.

In one or more embodiments, the sequence of updating the medical synchronization application between the cloud server and local servers is random. However, because the update file already exists in the cloud repository of the cloud server, the cloud server would always be the first to execute the update file and complete the update of the medical synchronization application. This enables the healthcare facilities to establish a continuous workflow in the event that a local server at one of the multiple healthcare facilities loses connection from the cloud when the cloud-based PACS system is updating the vendor-provided applications. For example, healthcare facilities that have completed the update of the vendor-provided application need not wait for the disconnected healthcare facility to complete the update of the vendor-provided application upon re-establishing connection with the cloud-based PACS system.

One or more embodiments of the invention may have one or more of the following advantages: the ability to automatically share and update medical images and data between multiple healthcare facilities that are in-network; the ability to maintain all of the local repositories of all of the in-network healthcare facilities that serve the same individual up-to-date with the individual's most recent medical images and data; the ability to establish a continuous workflow at every in-network healthcare facility without experiencing any downtime caused by a disconnection of any of the in-network healthcare facility with the share cloud; the ability to select the medical images and data to be stored in the local repositories of the respective in-network healthcare facilities so that the healthcare facilities would not need to maintain a full-sized on-site data center; the ability to automatically check for version mismatch to ensure that the synchronization and medical images and data processing settings of the devices connected to the cloud-based PACS are up-to-date and consistent; the ability to establish a continuous workflow at every in-network healthcare facility without experiencing any downtime caused by a disconnection of any of the in-network healthcare facility with the share cloud during an medical synchronization application update process; etc.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for updating a system that synchronizes medical data between a cloud repository on a cloud server and a plurality of local repositories on a plurality of local servers of healthcare facilities connected to the cloud server, the method comprising:

receiving, by the cloud server, a request to update a medical synchronization application stored on the cloud server and each of the local servers of the healthcare facilities using an update file;

transmitting, by the cloud server to each of the local servers, an instruction to update the medical synchronization application, wherein the instruction includes the update file;

determining, by the cloud server, a version information of the medical synchronization application on all of the local servers; and executing, by the cloud sever, the update file to update the medical synchronization application on the cloud server only in the event that cloud server determines that the medical synchronization application of all of the local servers have been updated; and in response to one of the plurality of local servers establishing a connection with the cloud server, causing the cloud server to:

determine the version information of the medical synchronization application of the local server establishing the connection; and in the event that the version information of the medical synchronization application of the local server establishing the connection is different from the version information of the medical synchronization application on the cloud server, transmit the instruction to update the medical synchronization application to the local server establishing the connection.

2. The method according to claim 1, further comprising:

in response to one of the plurality of local servers re-establishing a connection with the cloud server after being disconnected from the cloud server, causing the cloud server to:

determine the version information of the medical synchronization application on the local server establishing the connection; and in the event that the version information of the medical synchronization application on the local server re-establishing the connection is different from the version information of the medical synchronization application on the cloud server, transmit the instruction to update the medical synchronization application to the local server re-establishing the connection.

3. The method according to claim 2, wherein the local server establishing or re-establishing the connection to the cloud server is permitted to synchronize medical data with the cloud server only if the version information of the medical synchronization application on the local server establishing or re-establishing the connection is the same as the version information of the medical synchronization application on the cloud server.

4. The method according to claim 1, wherein each of the local servers is an application proxy server (APS) disposed in a medical facility.

5. The method according to claim 1, wherein the update file is stored in the cloud repository.

6. The method according to claim 1, wherein the request received by the cloud server includes the version information of the medical synchronization application, a date and time for the cloud server to execute the request, and a warning message that is included in the instruction transmitted to the local servers.

7. The method according to claim 6, wherein the request received by the cloud server is editable and scheduled by a user through a graphical user interface (GUI) displayed by a computer coupled to the cloud server.

8. The method according to claim 6 wherein the warning message is displayed in a pop-up window that appears on a display of a local computer coupled to the plurality of respective local servers.

9. The method according to claim 8, wherein the pop-up window includes a countdown timer that indicates a remaining time before the local servers will automatically execute the update file to update the medical synchronization application, and an additional warning message that notifies the user that the medical synchronization application will be automatically shut down when the countdown timer expires.

10. The method according to claim 6, wherein the request to update the medical synchronization application cannot be canceled once the cloud server executes the request.

11. The method according to claim 1, wherein each of the local servers is coupled to a local computer with a display, and the local computer is coupled to a modality in a medical facility.

12. The method according to claim 1, wherein the cloud repository on the cloud server is a repository for a cloud-based Picture Archiving and Communication System (PACS).

13. A non-transitory computer-readable medium (CRM) storing instructions that cause a cloud server coupled to a computer to perform an operation to update a system that synchronizes medical data between a cloud repository on the cloud server and a plurality of local repositories on a plurality of local servers of healthcare facilities connected to the cloud server, the operation comprising:

receiving, by the cloud server, a request to update a medical synchronization application stored on the cloud server and each of the local servers of the healthcare facilities using an update file;

transmitting, by the cloud server to each of the local servers, an instruction to update the medical synchronization application, wherein the instruction includes the update file;

determining, by the cloud server, a version information of the medical synchronization application on all of the local servers; and executing, by the cloud sever, the update file to update the medical synchronization application on the cloud server only in the event that cloud server determines that the medical synchronization application of all of the local servers have been updated; and in response to one of the plurality of local servers establishing a connection with the cloud server, causing the cloud server to:

determine the version information of the medical synchronization application of the local server establishing the connection; and in the event that the version information of the medical synchronization application of the local server establishing the connection is different from the version information of the medical synchronization application on the cloud server, transmit the instruction to update the medical synchronization application to the local server establishing the connection.

14. The CRM according to claim 13, wherein the operation further comprising:

in response to one of the plurality of local servers re-establishing a connection with the cloud server after being disconnected from the cloud server, causing the cloud server to:
- determine the version information of the medical synchronization application on the local server establishing the connection; and
- in the event that the version information of the medical synchronization application on the local server re-establishing the connection is different from the version information of the medical synchronization application on the cloud server, transmit the instruction to update the medical synchronization application to the local server re-establishing the connection.

15. The CRM according to claim 14, wherein the local server establishing or re-establishing the connection to the cloud server is permitted to synchronize medical data with the cloud server only if the version information of the medical synchronization application on the local server establishing or re-establishing the connection is the same as the version information of the medical synchronization application on the cloud server.

16. The CRM according to claim 13, wherein each of the local servers is an application proxy server (APS) disposed in a medical facility.

17. A system that synchronizes medical data, comprising:
a cloud server;
a cloud repository on the cloud server; and
a plurality of local repositories on a plurality of local servers of healthcare facilities connected to the cloud server,
wherein the cloud server:
- receives a request to update a medical synchronization application stored on the cloud server and each of the local servers using an update file,
- transmits, to each of the local servers, an instruction to update the medical synchronization application, wherein the instruction includes the update file,
- determines, a version information of the medical synchronization application on all of the local servers, and
- executes the update file to update the medical synchronization application on the cloud server only in the event that cloud server determines that the medical synchronization application of all of the local servers have been updated, and wherein, in response to one of the plurality of local servers establishing a connection with the cloud server, the cloud server:
- determines the version information of the medical synchronization application of the local server establishing the connection, and
- in the event that the version information of the medical synchronization application of the local server establishing the connection is different from the version information of the medical synchronization application on the cloud server, transmits the instruction to update the medical synchronization application to the local server establishing the connection.

18. The system according to claim 17, wherein in response to one of the plurality of local servers re-establishing a connection with the cloud server after being disconnected from the cloud server, the cloud server further:
- determines the version information of the medical synchronization application on the local server establishing the connection; and
- in the event that the version information of the medical synchronization application on the local server re-establishing the connection is different from the version information of the medical synchronization application on the cloud server, transmits the instruction to update the medical synchronization application to the local server re-establishing the connection.

19. The system according to claim 18, wherein the local server establishing or re-establishing the connection to the cloud server is permitted to synchronize medical data with the cloud server only if the version information of the medical synchronization application on the local server establishing or re-establishing the connection is the same as the version information of the medical synchronization application on the cloud server.

20. The system according to claim 17, wherein each of the local servers is an application proxy server (APS) disposed in a medical facility.

* * * * *